US009441033B2

(12) United States Patent
Benchikh et al.

(10) Patent No.: US 9,441,033 B2
(45) Date of Patent: Sep. 13, 2016

(54) DETECTION OF SYNTHETIC CANNABINOIDS

(75) Inventors: Elouard Benchikh, Crumlin (GB);
Stephen Peter Fitzgerald, Crumlin (GB); Paul John Innocenzi, Crumlin (GB); Philip Andrew Lowry, Crumlin (GB); Ivan Robert McConnell, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 446 days.

(21) Appl. No.: 13/585,643

(22) Filed: Aug. 14, 2012

(65) Prior Publication Data

US 2013/0196354 A1    Aug. 1, 2013

Related U.S. Application Data

(63) Continuation-in-part of application No. 13/332,042, filed on Dec. 20, 2011, now Pat. No. 8,906,633.

(30) Foreign Application Priority Data

Feb. 14, 2011    (GB) .................... 1102544.2
Jun. 21, 2011    (GB) .................... 1110425.4

(51) Int. Cl.
| C07K 16/16 | (2006.01) |
| C07K 16/44 | (2006.01) |
| C07K 17/14 | (2006.01) |
| G01N 33/94 | (2006.01) |
| C07D 209/12 | (2006.01) |

(52) U.S. Cl.
CPC ............ *C07K 16/16* (2013.01); *C07D 209/12* (2013.01); *C07K 16/44* (2013.01); *C07K 17/14* (2013.01); *G01N 33/948* (2013.01); *C07K 2317/33* (2013.01)

(58) Field of Classification Search
None
See application file for complete search history.

(56) References Cited

U.S. PATENT DOCUMENTS

| 5,817,766 | A | * | 10/1998 | Hui et al. .................... 530/387.1 |
| 6,900,236 | B1 | * | 5/2005 | Makriyannis et al. ....... 514/415 |
| 8,906,633 | B2 | | 12/2014 | Benchikh et al. |
| 2013/0065323 | A1 | | 3/2013 | Benchikh et al. |
| 2013/0066053 | A1 | * | 3/2013 | Fitzberald et al. ........ 530/389.8 |
| 2015/0118763 | A1 | | 4/2015 | Fitzgerald et al. |

FOREIGN PATENT DOCUMENTS

| EP | 0736529 A1 | 3/1996 |
| EP | 2487155 A1 | 8/2012 |
| WO | 02073214 A2 | 9/2002 |
| WO | 2010127452 A1 | 11/2010 |

OTHER PUBLICATIONS

C. V. Rao, "Immunology,. A textbook", Alpha Science Internatl. Ltd., 2005, pp. 63, 69-71.*
Dresen et al., "Monitoring of herbal mixtures potentially containing synthetic cannabinoids as psychoactive compounds," J. Mass Spectrometry, 2010, vol. 45, issue 10, pp. 1186-1194, Article first published online: Sep. 20, 2010.*
Sobolevsky et al., "Detection of JWH-018 metabolites in smoking mixture post-administration urine," Forensic Science International, 2010, vol. 200, issues 1-3, pp. 141-147, Article first published online: Apr. 28, 2010.*
De Jager et al., "LC-MS/MS method for the quantitation of metabolites of eight commonly-used synthetic cannabinoids in human urine—An Australian perspective," J. Chromatography B, 2012, vol. 897, pp. 22-31, Article first published online: Apr. 9, 2012.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Randox Toxicology, Product List 2012, pp. 1-4.
Watanabe, K., et al., "Cross-Reactivity of Various Tetrahydrocannabinol Metabolites with a Monoclonal Antibody against Tetrahydrocannabinolic Acid," Journal of Health Science, (2000), vol. 46, No. 4, pp. 310-313.
Tanaka, H., et al., "Monoclonal antibody against tetrahydrocannabionolic acid distinguishes Cannabis sativa samples from different plant species," Forensic Science International (1999), vol. 106, pp. 135-146.
Salamone, S., et al., "A Non-Cannabinoid Immunogen Used to Elicit Antibodies with Broad Cross-Reactivity to Cannabinoid Metabolites," Journal of Forensic Sciences, pp. 821-826, 1998, vol. 43, No. 4.
Tanaka, H., "Immunochemical Approach Using Monoclonal Antibody against •9-TetrahydrocannabinolicAcid (THCA) to Discern Cannabis Plants and to Investigate New Drug Candidates," Current Drug Discovery Technologies, (2011) vol. 8, pp. 3-15.
Dresen, S., et al., "Development and validation of a liquid chromatography—tandem mass spectrometry method for the quantitation of synthetic cannabinoids of the aminoalkylindole type and methanandamide in serum and its application to forensic samples," J. Mass Spectrom, (2011), vol. 46, pp. 163-171.
Logan, B., et al., "Technical Bulletin: NMS Labs test for JWH-018, JWH-019, JWH-073, JWH-250 and AM-2201 Primary Monohydroxy Metabolites in Human Urine," NMS Labs, (2011), pp. 1-5.
Logan, B., et al., "Identification of Synthetic Cannabinoids in Herbal Incense Blends in the United States," Forensic Sciences, (2012), vol. 57, No. 5, pp. 1168-1180.
Hudson, S. et al., "Use of High-Resolution Accurate Mass Spectrometry to Detect Reported and Previously Unreported Cannabinomimetics in 'Herbal High' Products," J. Anal. Toxicol., 2010, pp. 252-260, vol. 34.

(Continued)

*Primary Examiner* — Galina Yakovleva
(74) *Attorney, Agent, or Firm* — Saul Ewing LLP; Kathryn Doyle; Domingos J. Silva

(57) ABSTRACT

The invention describes methods and kits for detecting and determining current and future synthetic cannabinoids from the JWH and RCS families. Unique antibodies derived from novel immunogens enable said methods and kits.

5 Claims, 16 Drawing Sheets

(56) References Cited

OTHER PUBLICATIONS

Huffman, J. et al., "1-Pentyl-3-phenylacetylindoles, a New Class of Cannabimimetic Indoles," Bioorganic & Medicinal Chemistry Letters, 2005, pp. 4110-4113, vol. 15.

Kraemer, T., "V10—Studies on the Metabolism of JWH-18, the Pharmacologically Active Ingredient of Different Misused Incenses," Abstracts—Vortrage Hauptsymposium, 2008, pp. 90, vol. 76, No. 2.

Liu, Y. et al., "Design and Synthesis of AX4697, a Bisindolylmaleimide Exo-affinity Probe that Labels Protein Kinase C Alpha and Beta," Bioorganic & Medicinal Chemistry Letters, 2008, pp. 5955-5958, vol. 18.

Melvin, L.S. et al., "A Cannabinoid Derived Prototypical Analgesic," J. Med. Chem., 1984, vol. 27, No. 1, pp. 67-71.

Möller, I. et al., "Screening for the Synthetic Cannabinoid JWH-018 and Its Major Metabolites in Human Doping Controls," Drug Testing and Analysis, 2011, pp. 609-620, vol. 3.

Rana, S. et al., "Routine Screening of Human Urine for Synthetic Cannabinoids by LC-MS/MS Utilizing Spectrum Based Library Search," Redwood Toxicology Laboratory, Soft 2010. (Abstract).

Singh, P. et al., "Synthesis and Evaluation of Indole-based New Scaffolds for Antimicrobial Activities—Identification of Promising Candidates," Bioorganic & Medicinal Chemistry Letters, 2011, pp. 3367-3372, vol. 21.

Uchiyama, N. et al., "Chemical Analysis of Synthetic Cannabinoids as Designer Drugs in Herbal Products," Forensic Science International, 2010, pp. 31-38, vol. 198.

Weissman, A. et al., "Cannabimimetic Activity from CP-47,497, a Derivative of 3-Phenylcyclohexanol," J. Pharmacol. Exp. Ther, 1982, vol. 223, No. 2, pp. 516-523.

Wild, D. (editor), The Immunoassay Handbook, Third Edition, Elsevier Ltd., 2005, pp. 255-256.

Wintermeyer, A. et al., "In vitro Phase I Metabolism of the Synthetic Cannabimimetic JWH-018," Anal. Bioanal. Chem., 2010, pp. 2141-2153, vol. 398.

Zhao, D. et al., "Synthesis of Phenol, Aromatic Ether, and Benzofuran Derivatives by Copper-Catalyzed Hydroxylation of Aryl Halides," Angew. Chem. Int. Ed., 2009, pp. 8729-8732, vol. 48, Issue 46.

* cited by examiner

RCS-4 N-(5-hydroxypentyl) metabolite

RCS-4 N-(5-carboxypentyl) metabolite

RCS-4 N-(4-hydroxypentyl) metabolite

DETECTION OF SYNTHETIC CANNABINOIDS

CROSS-REFERENCE TO RELATED APPLICATIONS

This application is a continuation-in-part of, and claims priority to, U.S. patent application Ser. No. 13/332,042, filed Dec. 20, 2011, now issued as U.S. Pat. No. 8,906,633, which claims priority to Great Britain Patent Applications No. 1102544.2, filed Feb. 14, 2011, and No. 1110425.4, filed Jun. 21, 2011, all of which applications are hereby incorporated by reference in their entireties.

BACKGROUND

The increasing rise in the use of stealth drugs (novel synthetic drugs that were previously or remain analytically/structurally uncharacterised and unclassified by government institutions), is exemplified by synthetic cannabinoid products which incorporate JWH-018 as the active ingredient. Stealth synthetic cannabinoid (SSC) drug manufacturers can base their choice of active molecular target on scientific literature studies that address the therapeutic potential of $CB_1$ (the CNS cannabinoid receptor) agonists and antagonists. By incorporating novel, analytically uncharacterised compounds with high $CB_1$ receptor affinity into herbal mixtures (packaged under such names as Spice, Yucatan Fire), the manufacturers are able to legally target drug consumers clandestinely by promoting the material as herbal therapeutics. A problem for governments and drug enforcement agencies is that even after identifying and banning a new synthetic cannabinoid, the manufacturers can rapidly react to the banning by incorporating a different active analogue into the same or a different herbal product; targeted minor changes in the molecular structure of the known active compound can preserve receptor activity but often produces a molecule whose GC-MS/LC-MS (the commonly applied detection techniques) profile is completely different from the original active molecule. Hence the new active molecule initially remains unidentified and a further resource intensive and costly chemical analytical study to enable structural characterisation is required. The main active ingredients highlighted in SSC products to date are JWH-018, CP 47,497 and JWH-073 (Uchiyama et al. 2010; Hudson et al. 2010; Dresen et al. 2010). Initial studies of the metabolism of JWH compounds have highlighted metabolic processes similar to tetrahydrocannabinol (THC) metabolism, namely ring and alkyl substituent hydroxylation, carboxylation and glucuronidation. As described herein, unless otherwise stated, JWH refers to molecules comprising structure I which are $CB_1$-active or metabolites of the $CB_1$-active parent, in which the indole ring system is present as a fused heterobicyclic i.e. it is not part of, for example, a fused heterotricyclic ring system. Y can be hydrogen or a substituted or unsubstituted alkyl group such as butyl, pentyl or 2-(morpholin-4-yl)ethyl, while R is a carbon atom which may be part of a fused or unfused, substituted or unsubstituted aromatic ring or a substituted or unsubstituted alkyl, alkenyl or alkynyl chain optionally attached to a fused or unfused, substituted or unsubstituted aromatic ring, but is usually a substituted or unsubstituted naphthyl ring.

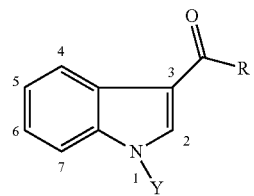

Structure I

Indolyl, naphthyl, carboxyalkyl, N-dealkylated and N-alkyl mono-, di-, and tri-hydroxylated metabolites, as well as their glucuronidated conjugates are reported JWH-018 metabolites (Sobolevsky et al. 2010; Kraemer et al. 2008). Moller et al. (2010) highlighted the same metabolites as Sobolevsky et al. (2010), with the monohydroxylated N-alkyl chain being the most abundant phase I metabolite; Wintermeyer et al. (2010) conducted an in vitro study that largely confirmed previous findings. Herbal therapeutics have been analysed using solvent extraction, pre-derivatisation and finally GC-MS analysis in SIM mode (Rana et al. 2010). This method is inadequate for the detection of future and 'current' JWH SSCs (it is conceivable that 'current' herbal therapeutics, as well as JWH-018, incorporate JWH a SSCs that are not yet characterised), requires sample pre-derivatisation, specialist staff for its implementation and expensive equipment. In order to address the problem associated with the cheap and rapid detection of known JWH molecules and their metabolites and/or future and associated metabolites based on the JWH drug families, the Inventors devised a novel method based on novel antibodies raised from novel immunogens. The antibodies underpin an effective analytical and economic solution to the detection and quantification of current and future JWH $CB_1$-active molecules in in vitro patient samples and herbal therapeutics.

SUMMARY OF THE INVENTION

The invention describes a rapid and practical method for the detection and determination of known and/or stealth synthetic cannabinoids based on the JWH and/or RCS drug families. Kits and their use for JWH or RCS SSC detection and determination in herbal therapeutics and in vitro patient samples are also described. The invention is underpinned by novel immunogens and antibodies which enable said methods, kits and applications.

0l5. 6 contains diagrams of chemical structures of JWH-015, JWH-016 and JWH-007.

Figure 7:
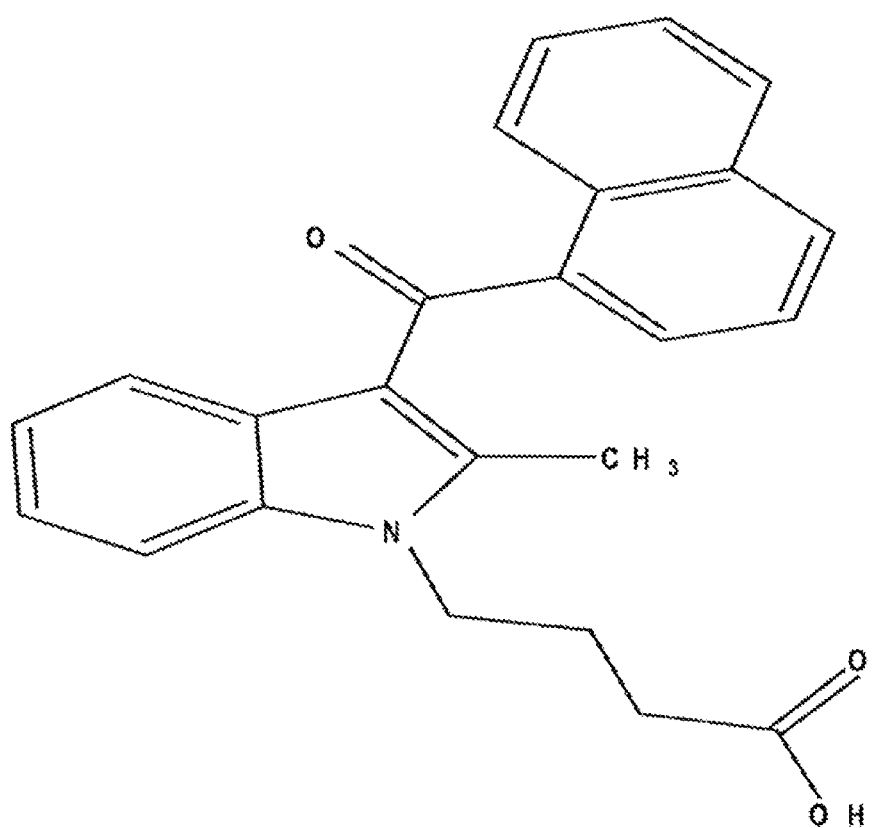

FIG. 7 contains diagrams of 4-(3-(1-naphthoyl)-2-methyl-1H-indol-1-yl)butanoic acid.

Figure 8:
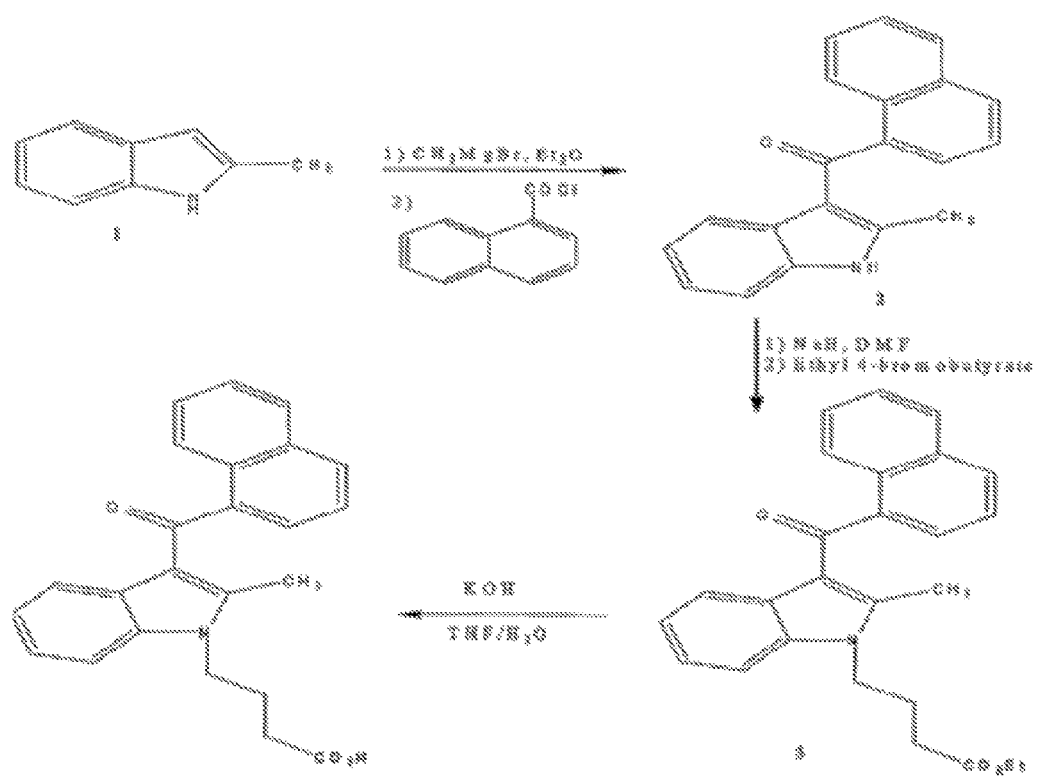

FIG. 8 is a diagram of a reaction for the preparation of 4-(3-(1-naphthoyl)-2-methyl-1H-indol-1-yl)butanoic acid.

Figure 9:
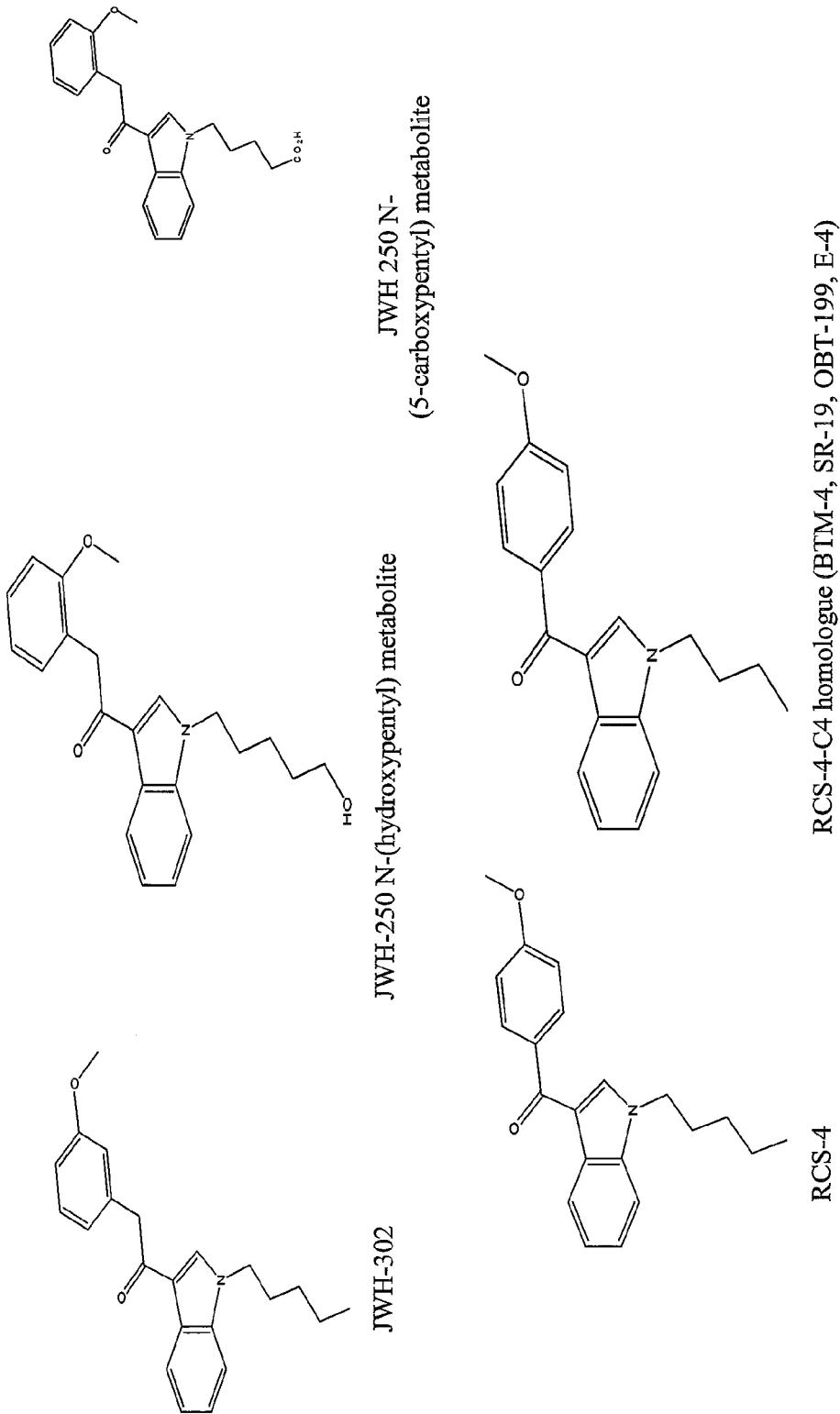
Figure 9:
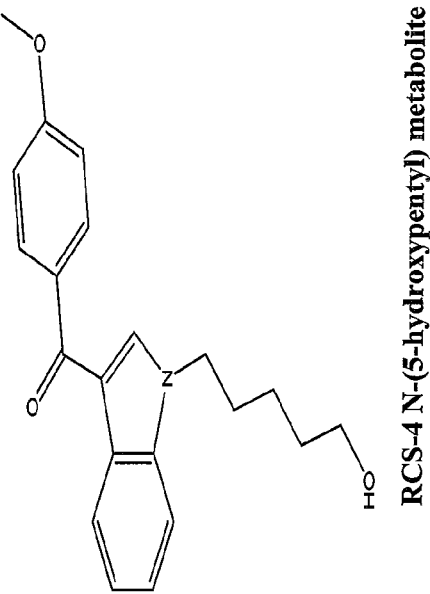
Figure 9:
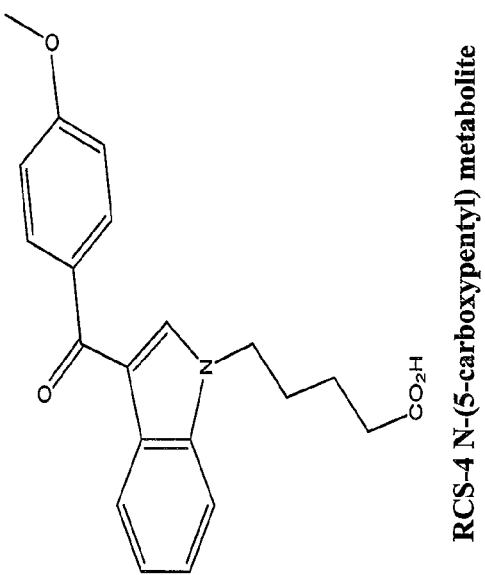
Figure 9:
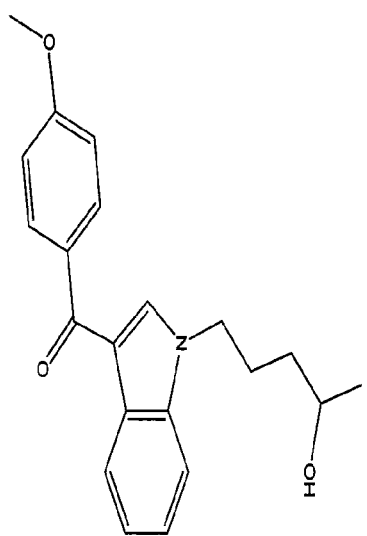

FIG. 9 illustrates chemical structures of JWH-203, JWH-302 JWH-250, JWH-250 N-(5-hydroxypentyl) metabolite, JWH-250 N-(5-carboxypentyl) metabolite, JWH-251, RCS-4, RCS-4-C4 homologue, RCS-4 N-(4-hydroxypentyl) metabolite, RCS-4 N-(5-hydroxypentyl) metabolite and RCS-4 N-(5-carboxypentyl) metabolite.

Figure 10:
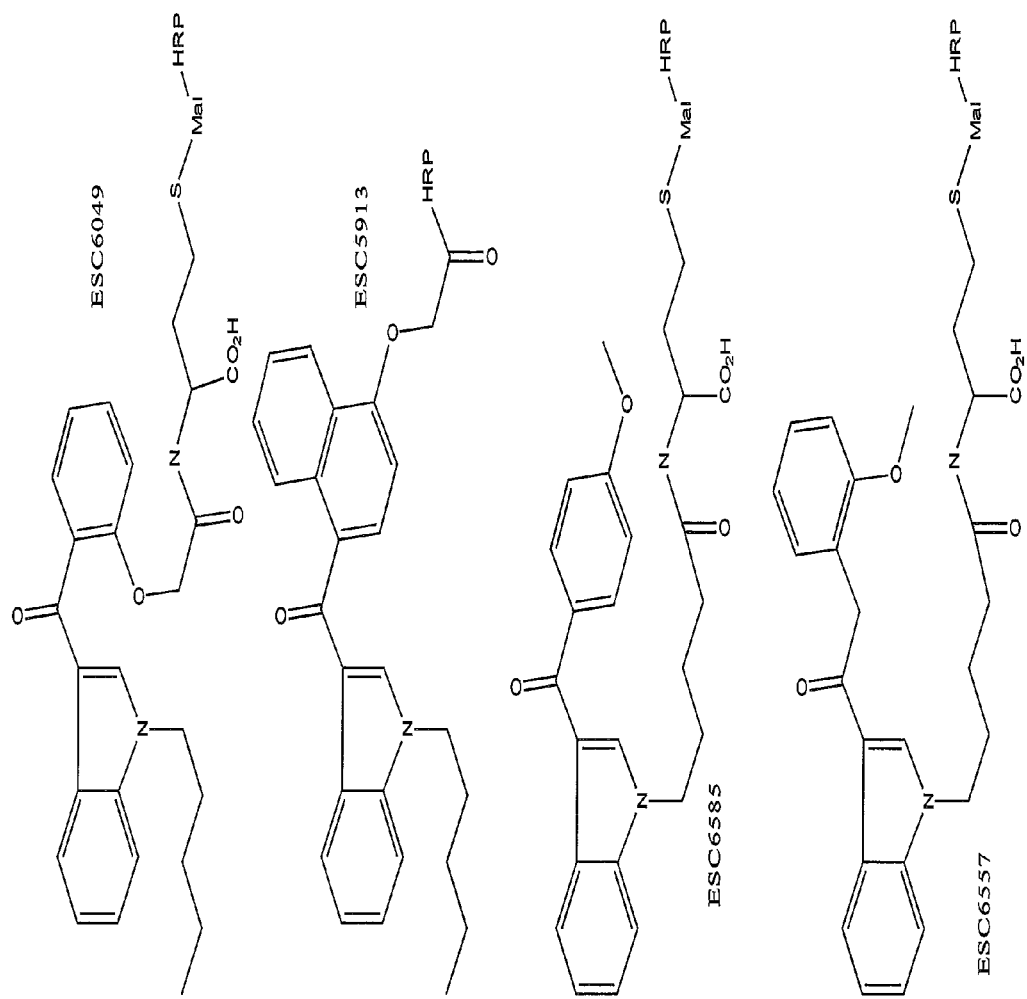
Figure 10:
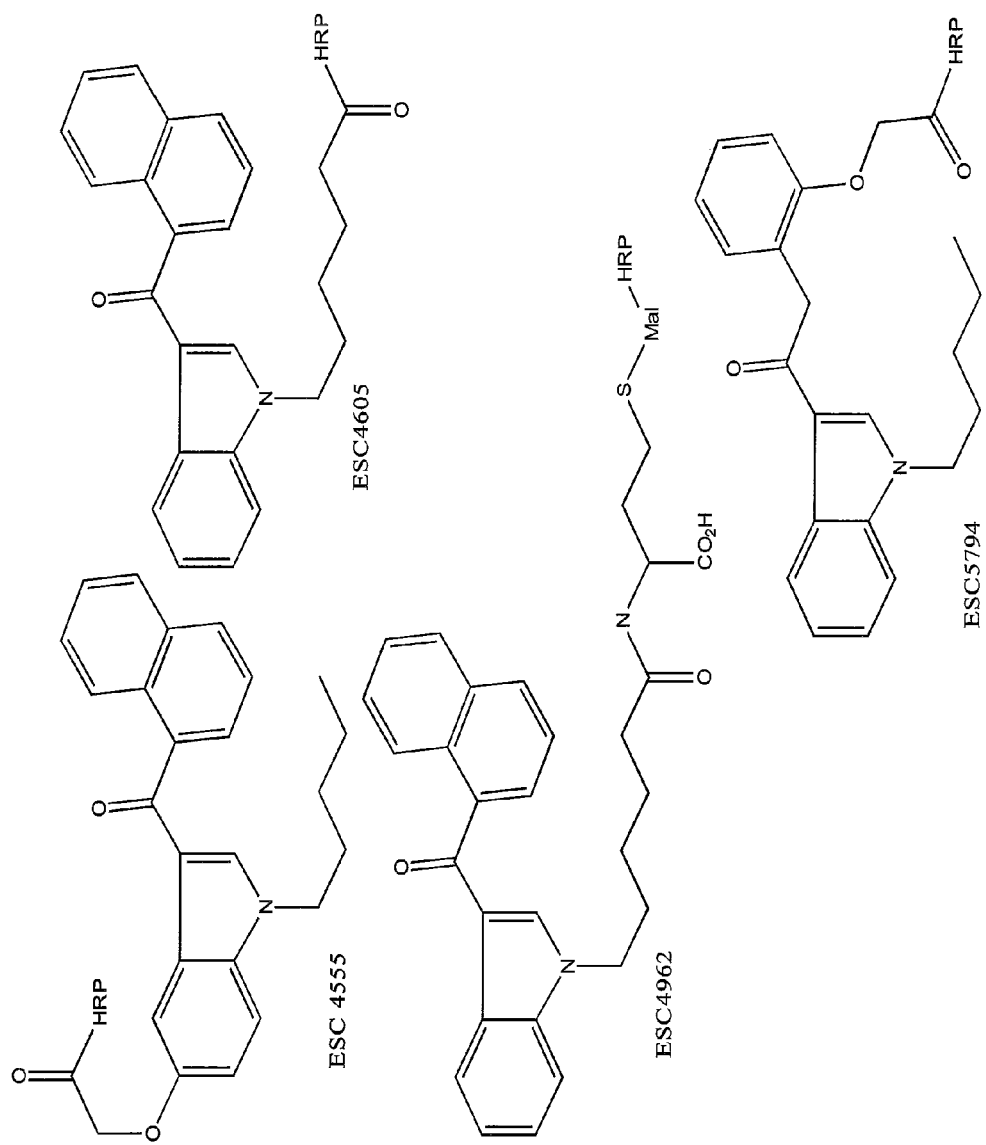
Figure 10:
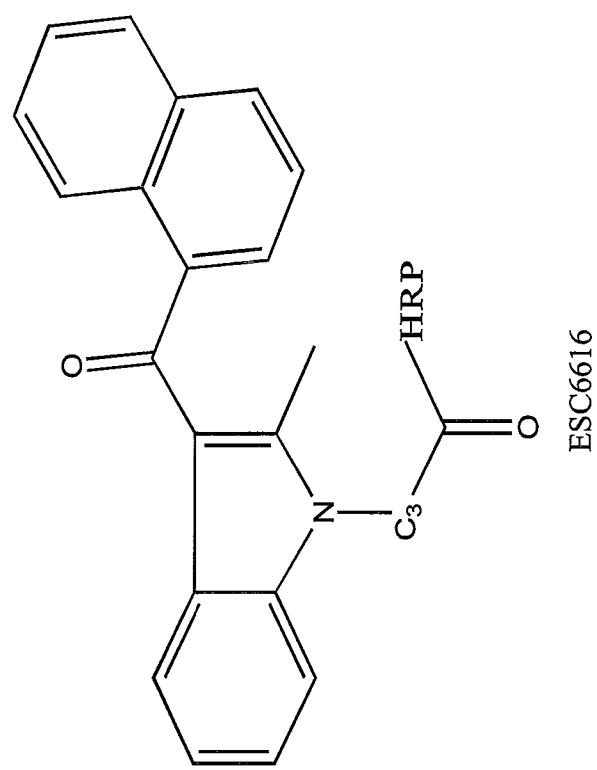

FIG. 10 illustrates chemical structures of tracers.

Figure 11:
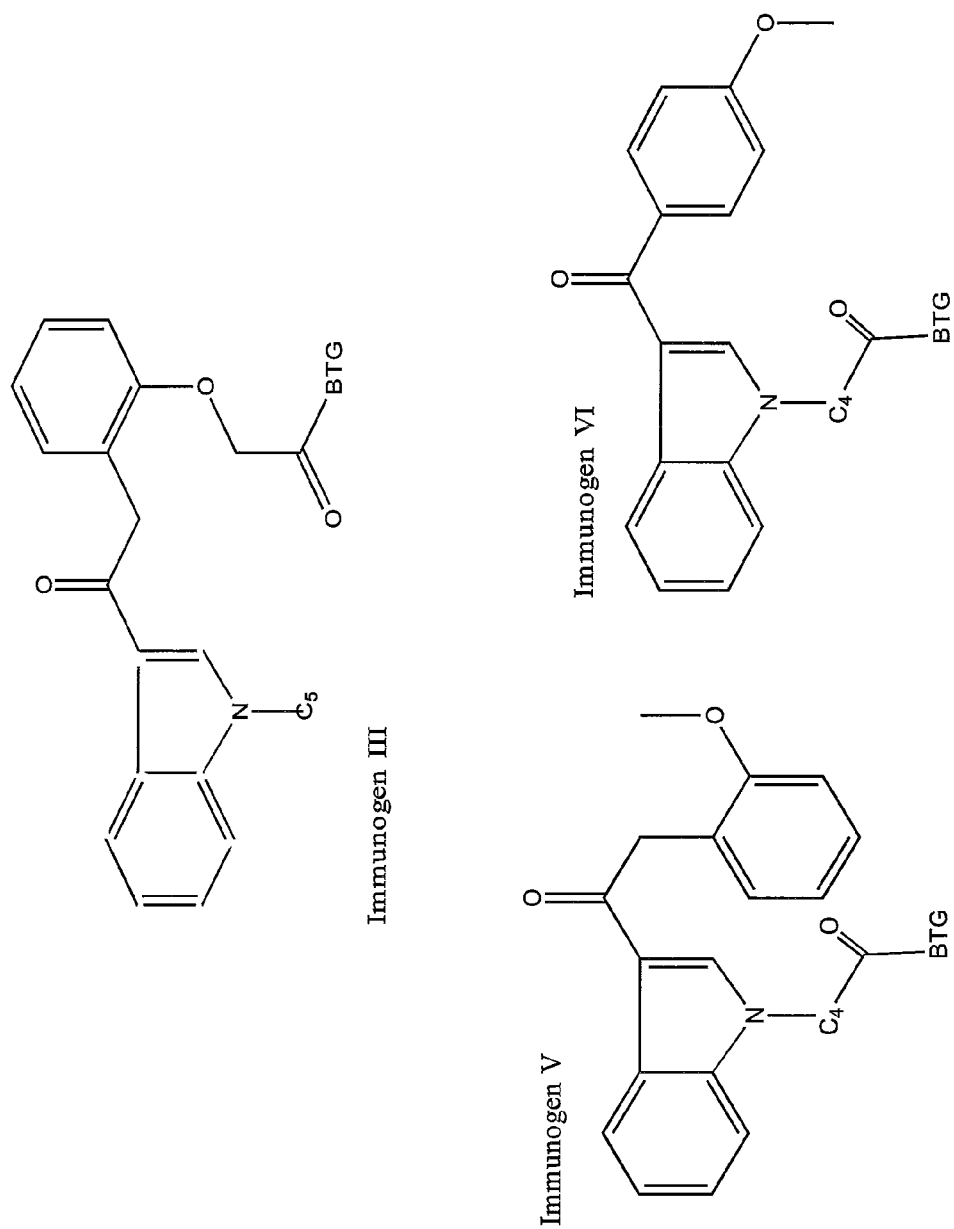

FIG. 11 illustrates chemical structures of immunogens.

DETAILED DESCRIPTION OF THE INVENTION

It has been found that immunogens of the invention raise antibodies that are able to bind to several JWH or RCS molecules and metabolites. The skilled person is aware that for these antibodies to recognize JWH or RCS molecules they must bind to particular structures or epitopes of the hapten (in this context the hapten being that part of the immunogen that is not the crosslinker or accm); the epitopes are often distinct groups incorporating functional groups. In a first aspect, the invention provides an antibody which binds to an epitope of structure

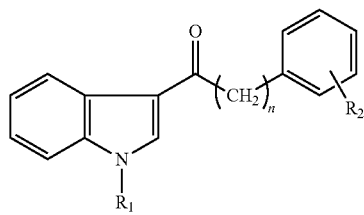

wherein,
$R_1$ is a $C_2$-$C_5$ substituted or unsubstituted, hydrocarbon chain;
$R_2$ is methoxy, $CH_3$ or chlorine.

Optionally, the antibody binds to an epitope of structure

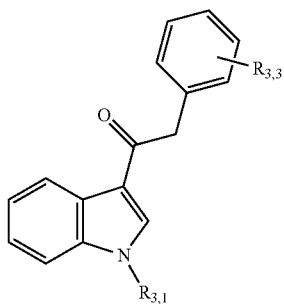

wherein,
$R_{3,1}$ is pentyl; and
$R_{3,3}$ is methoxy, $CH_3$ or chlorine, optionally at the ortho or meta position on the phenyl ring. Further optionally, the antibody binds to an epitope selected from the group consisting of the molecules JWH-203, JWH-250, JWH-251 and JWH-302. Still further optionally, the antibody of claim 3 is characterised by being raisable from an immunogen of structure III and/or having a $B/B_0$ of ≤20% (standardised with JWH-250 and using tracer ESC6557).

Alternatively, the antibody of claim 1 binds to an epitope of structure

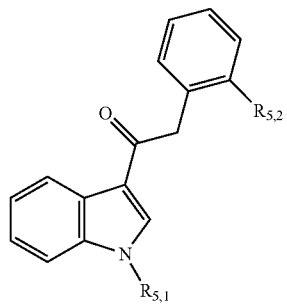

wherein,
$R_{5,1}$ is a $C_2$-$C_5$ substituted or unsubstituted, hydrocarbon chain;
$R_{5,2}$ is methoxy, $CH_3$ or chlorine. Optionally, $R_{5,1}$ is selected from substituted ethyl, optionally 2-ethyl-cyclohexyl; substituted butyl, optionally butyryl; pentyl; and substituted pentyl, optionally 5-hydroxypentyl. Further optionally, the antibody of claim 6 binds to an epitope selected from the group consisting of the molecules JWH-203, JWH-250, JWH-250 N-(5-hydroxypentyl) metabolite, JWH-250 N-(5-carboxypentyl) metabolite, JWH-251 and RCS-8. Further optionally, the antibody is further characterised by being raisable from an immunogen of structure V and/or having a $B/B_0$ of ≤16% (standardised with RCS-8 and using tracer ESC6557).

Alternatively, the antibody binds to an epitope of structure

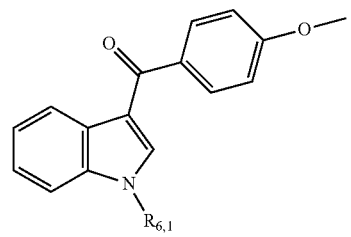

wherein,
$R_{6,1}$ is a $C_4$ or $C_5$ substituted or unsubstituted hydrocarbon chain. Optionally, $R_{6,1}$ is selected from butyl; pentyl; and substituted pentyl, optionally selected from 4-hydroxypentyl, 5-hydroxypentyl and 4-carboxypentyl. Further optionally, the antibody binds to an epitope of the molecules RCS-4, RCS-4-C4 homologue, RCS-4 N-(4-hydroxypentyl) metabolite, RCS-4 N-(5-hydroxypentyl) metabolite and RCS-4 N-(5-carboxypentyl) metabolite. Still further optionally, the antibody is characterised by being raisable from an immunogen of structure VI and/or having a $B/B_0$ of ≤15% (standardised with RCS-4 and using tracer ESC6585).

A further aspect of the invention is an antibody raised against the above-mentioned immunogen, that is able to bind to molecules of the JWH or RCS families and their metabolites. The term 'able to bind to', as used herein, does not imply that the antibodies have a choice of whether or not to bind to the JWH or RCS molecules, but that under standard immunoassay conditions the antibodies will bind to the JWH or RCS molecules. The antibodies also have the potential to bind to $CB_1$-active derivatives of JWH molecules that could represent future generations of SSCs.

Optionally, the antibodies may have broad cross-reactivity across the JWH or RCS families and metabolites. For example, without intending to limit the invention thereto, antibodies raised to.

When used in reference to an antibody, the word specific in the context of the current invention refers to the analyte that is preferably bound by the antibody, as gauged by a suitable metric such as the $IC_{50}$. Given the $IC_{50}$ of various analytes their cross-reactivities can be calculated. The antibody can either be a polyclonal or monoclonal antibody using well-known methods. If the polyclonal antibody possesses the required specificity and sensitivity, that is, it binds a single analyte within the detection range of the assay, development of a monoclonal antibody is unnecessary. Alternatively, a polyclonal or monoclonal antibody that binds to several analytes might be desirable; in the context of the current invention antibodies that bind several analytes are preferred. One or more antibodies of the invention can be incorporated into a kit for the detection and determination of individual or multiple SSCs. The skilled person in the immunodiagnostic field is aware of several alternative immunoassay formats that could incorporate the antibodies of the invention either in solution or tethered (e.g. covalently bonded or electrostatically 'non-bonded' through Van der Waal's forces) to a solid substrate such as beads, glass/plastic slides or ceramic chips (a chip defined as a small, planar substrate). A preferred solid substrate onto which the antibodies of the invention are covalently bonded is a chip, preferably a ceramic chip; the word 'biochip' can be used to refer to a chip with antibodies attached. Such a "biochip" is described in EP1273349, incorporated herein by reference its entirety. Thus the invention also provides a solid substrate, preferably a biochip, comprising antibodies raised to an immunogen of one or more of structures (a), (b), (c), (d), (e), (f), (g) or (h), the antibodies being able to bind to an epitope of one or more molecules of the JWH family and/or CP family and/or one or more metabolites thereof. The antibodies of the invention can be used for the detection or determination of a single SSC such as JWH-018, either as the parent molecule or as a metabolite, but a preferred embodiment is the use of one or more antibodies, preferably two or more antibodies, at least one derived from Group I and one derived from Group II, for the detection or determination of several SSCs and/or their metabolites from the JWH and CP families. The detection and determination criteria for a SSC using an immunoassay platform includes, as is well-known in the art, exceeding a pre-defined cut-off/concentration value or measuring the calibrator equivalent value as derived from a calibrator curve (also referred to as a standard curve).

Classification of immunoassays depends on whether one (noncompetitive) or two (competitive) antigens are used:
1. Competitive, Homogeneous Immunoassay The antigen in the unknown sample competes with labeled antigen to bind with antibodies. The amount of unbound, labeled antigen is then measured, which is directly proportional to the concentration of sample antigen.
2. Competitive, Heterogeneous Immunoassay The antigen in the unknown sample competes with labeled antigen to bind with antibodies. The amount of labeled antigen bound to the antibody site is then measured. In this method, the response will be inversely related to the concentration of antigen in the unknown.
3. One-Site, Noncompetitive Immunoassay The unknown antigen in the sample binds with labeled antibodies. The unbound, labeled antibodies are washed away, and the bound, labeled is measured, which is directly proportional to the amount of unknown antigen.
4. Two-Site, Noncompetitive Immunoassays The antigen in the unknown sample is bound to the antibody site, then labeled antibody is bound to the antigen. The amount of labeled antibody on the site is then measured. It will be directly proportional to the concentration of the antigen because labeled antibody will not bind if the antigen is not present in the unknown sample. This type is also known as sandwich assay as the antigen is "sandwiched" between two antibodies.

Another aspect of the invention is a method of detecting or determining synthetic cannabinoids of the JWH or RCS families and their metabolites in an in vitro sample of an individual or in a solution derived from a substance suspected of containing synthetic cannabinoids comprising: contacting the sample or solution with one or more detecting agents and one or more antibodies of the invention that bind to molecules of the JWH or RCS families, measuring the detecting agents, and detecting or determining, by reference to calibrators, the presence or concentration of a molecule or molecules of the JWH or RCS families.

Optionally, the method further comprises a step of measuring the detecting agents before detecting or determining, by reference to calibrators, the presence or concentration of a molecule or molecules of the CP family. The detecting agents measuring step can be measuring detecting agent bound to the antibodies, the detecting agent being labeled antigen in a competitive, homogeneous immunoassay in which unbound, labeled antigen is measured. Alternatively, the detecting agents measuring step can be measuring detecting agent bound to the antibodies, the detecting agent being labeled antigen in a competitive, heterogeneous immunoassay in which bound, labeled antigen is measured. Further alternatively, the detecting agents measuring step can be measuring detecting agent bound to the antibodies, the detecting agent being labeled antibodies in a one-site, noncompetitive immunoassay in which bound, labeled antibodies are measured. Still further alternatively, the detecting agents measuring step can be measuring detecting agent bound to the antibodies, the detecting agent being labeled antibody that is bound to the antigen that is, in turn, also bound to the antibody.

With reference to 'detecting or determining', 'detecting' means qualitatively analyzing for the presence or absence of a substance, 'determining' means quantitatively analyzing for the amount of a substance.

Optionally, the detecting agent is a small molecule, generally of similar structure to a molecule to be detected conjugated to a labelling agent, the detecting agent being able to bind to one of the antibodies of the invention. The labelling agent is selected from an enzyme, a luminescent substance, a radioactive substance, or a mixture thereof. Preferably, the labelling agent is an enzyme, preferably a peroxidase, more preferably horseradish peroxidase (HRP). Alternatively, or additionally, the luminescent substance may be a bioluminescent, chemiluminescent or fluorescent material. For the purposes of the invention, the patient sample to be used for in vitro analysis can be hair or a peripheral biological fluid but is preferably whole blood, serum, plasma, or urine.

When referring to the detection or determination of a JWH or RCS molecule, with or without a suffixed number attached to JWH and RCS, the metabolite or metabolites are also inferred unless otherwise stated.

The invention also describes kits for detecting or determining a molecule or molecules of the JWH family and/or RCS family comprising one or more antibodies of the invention. Preferably, the kit comprises one or more antibodies raised to an immunogen of.

The antibodies of the kit are preferably tethered to any suitable solid support such as a chip. Although the solid support can be of any suitable shape such as a bead or a slide and of any suitable material such as silicon, glass or plastic, the solid support is preferably a ceramic chip. The kit may further include calibrators and one or more detecting agents and optionally includes instructions for the use of the antibodies of the kit and if incorporated, the calibrators and detecting agents, for detecting and determining molecules from the JWH and/or RCS families. The invention also embodies solid supports comprising the novel antibodies.

The antibodies of the invention are used for the detection or determination of JWH and/or RCS molecules either in herbal mixtures, an in vitro sample taken from an individual or any other substance suspected of their incorporation. A preferred use of the antibodies of the invention is their use in the detection and/or quantification of members of the JWH and/or RCS families and its metabolites in in vitro samples taken from individuals.

General Methods, Examples and Results
Preparation of Haptens, Immunogens and Detecting Agents Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen.

The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof.

Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

EXAMPLES

Immunogens III and V

Figure 4:
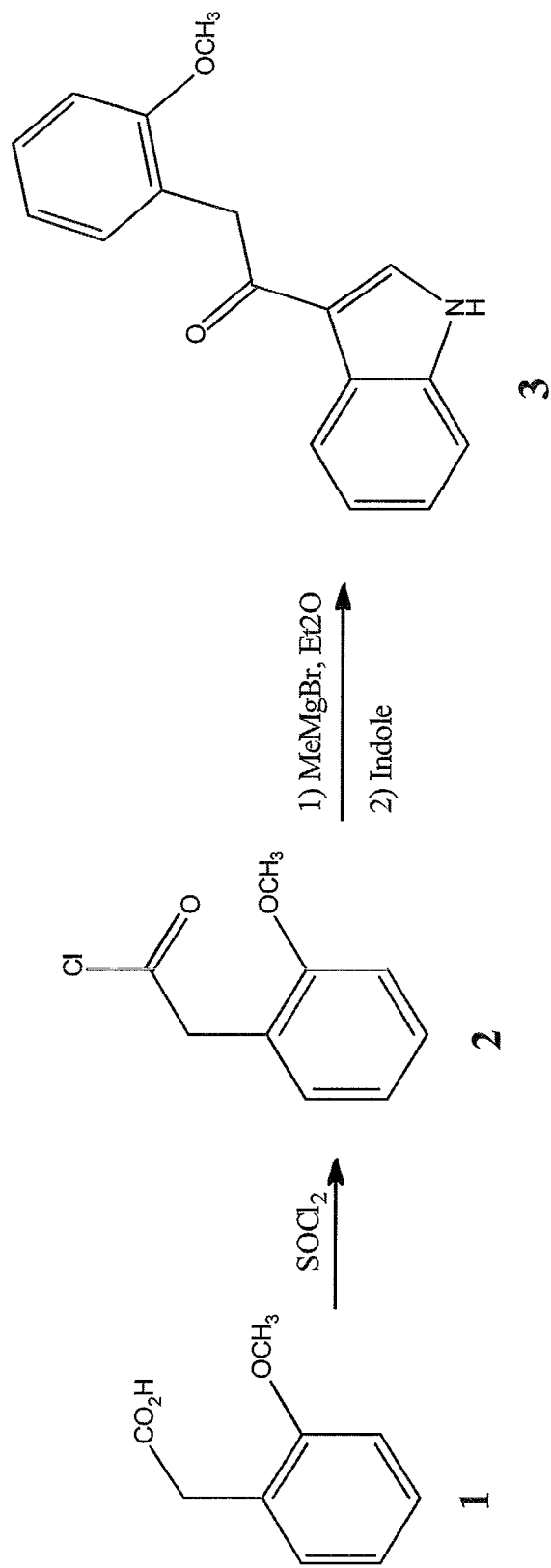
FIG. 4 contains diagrams of chemical reactions of the synthesis of Hapten-1—used to prepare Immunogen III.
Figure 4:
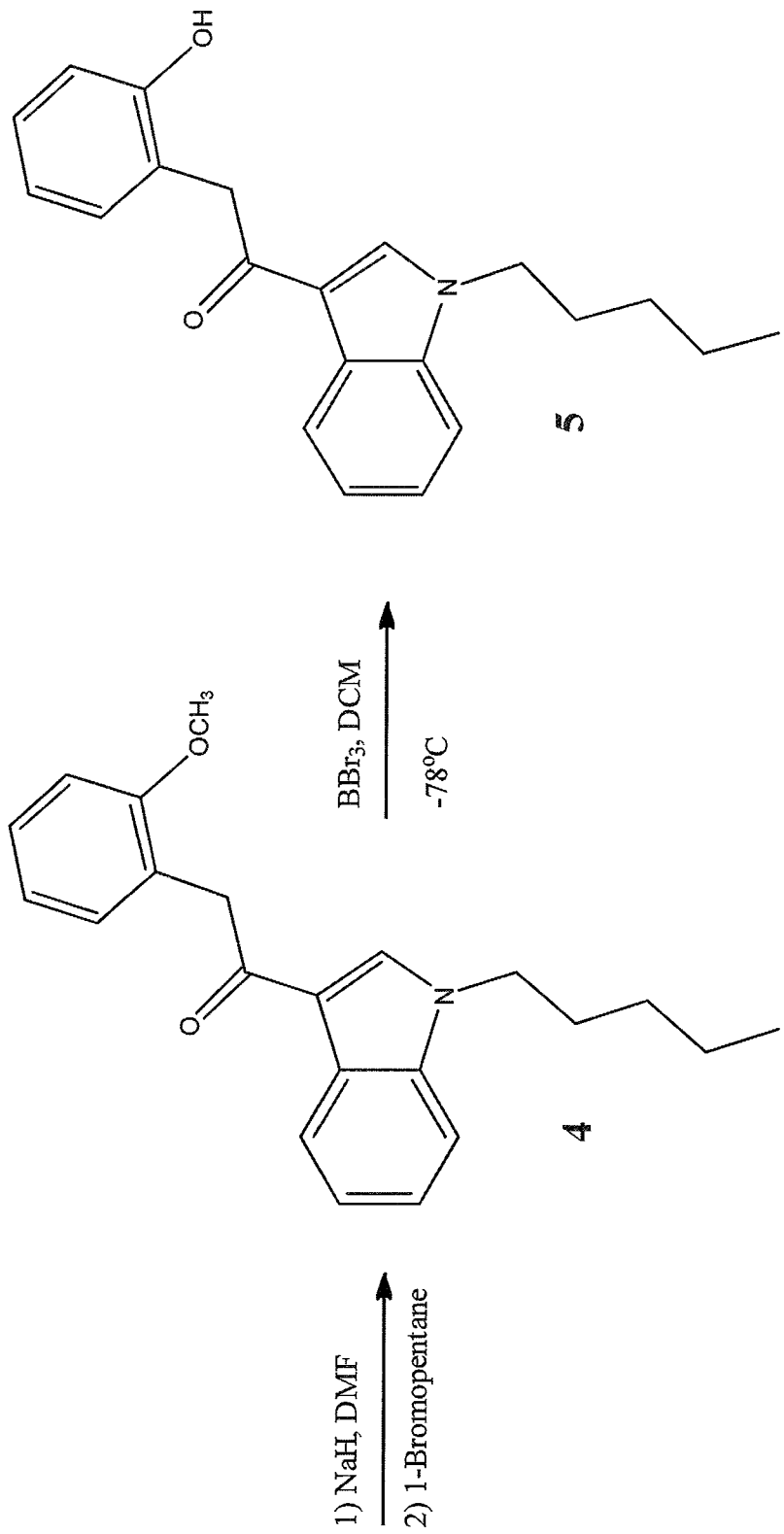
Figure 4:
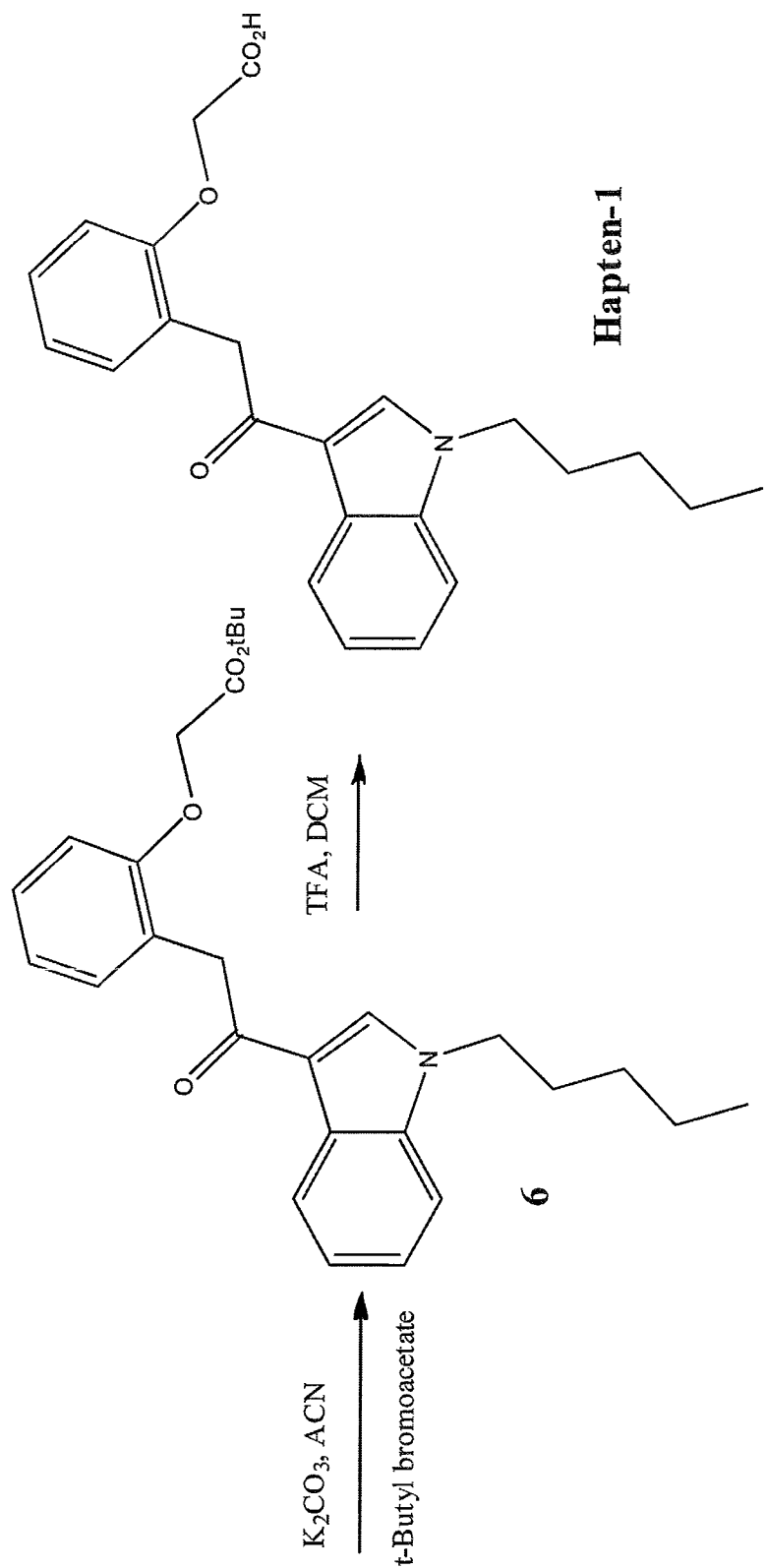
Figure 5:
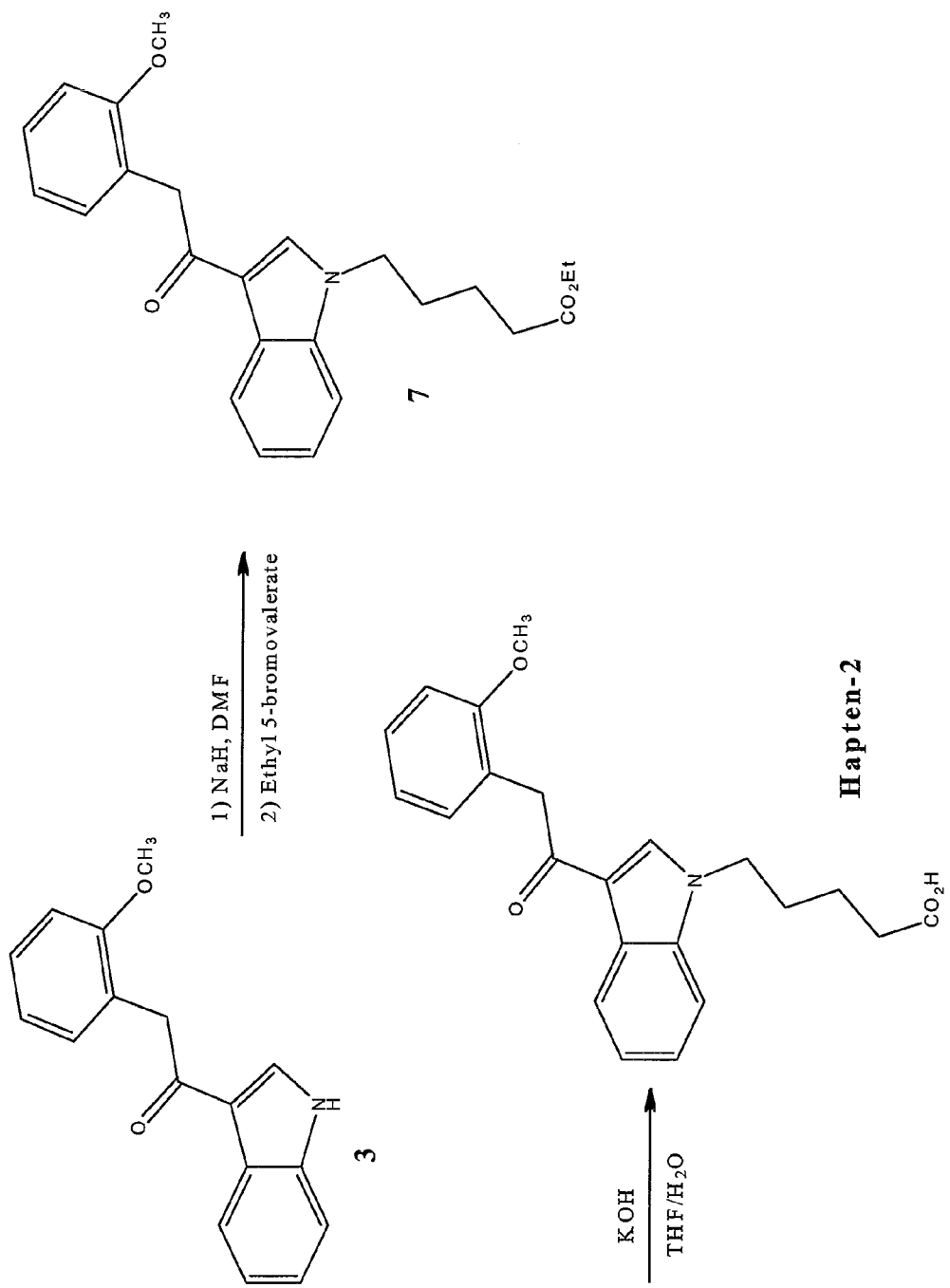
FIG. 5 contains diagrams of chemical reactions of the Synthesis of Hapten-2—used to prepare Immunogen V.
Figure 6:
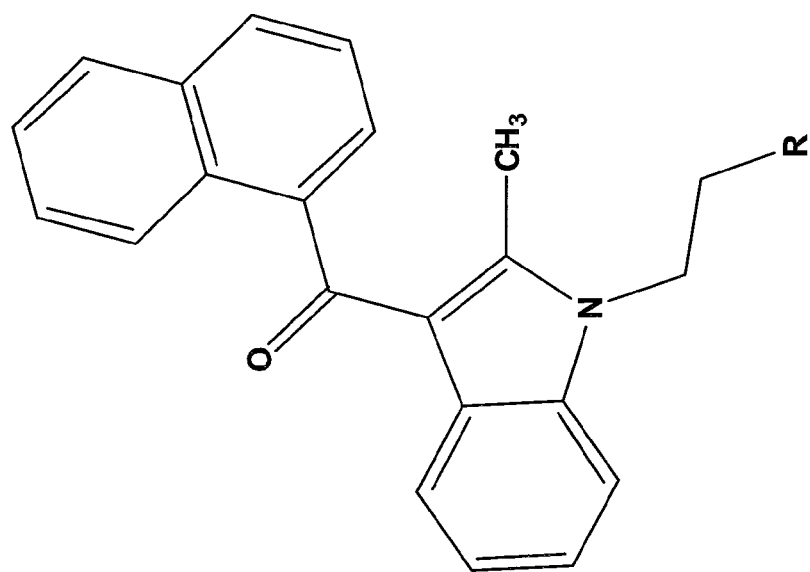

Prepared from Haptens 1 and 2 of FIGS. 4 and 5, Respectively

Example 1

Preparation of 2-methoxybenzoyl chloride 2

2-Methoxyphenylacetic acid 1 (16.6 g, 0.1 mol) was dissolved in thionyl chloride (100 ml) and refluxed for 90 min, and then the solvent was removed under vacuo and azeotroped twice with benzene (2×100 ml) to give 18.46 g (100%) of 2-methoxybenzoyl chloride 2 as a dark oil.

Example 2

Preparation of 1-(1H-indol-3-yl)-2-(2-methoxyphenyl)ethanone 3

Indole (11.7 g, 100 mmol) was dissolved in diethylether (100 ml) under nitrogen atmosphere and cooled to 0° C. 3M MeMgBr solution (35 ml, 105 mmol) was added dropwise and allowed to stir at room temperature for 2 hours. The reaction mixture was cooled at 0° C. and a solution of 2-methoxybenzoyl chloride 2 (18.46 g, 100 mmol) in diethyl ether (100 ml) was added dropwise with vigorous stirring. The reaction mixture was then allowed to stir at room temperature for 2 hours. A solution of ammonium chloride (300 ml) was added to the reaction mixture and the resulting mixture was stirred at room temperature overnight. The solid that was formed was collected by filtration, washed with water and hexane then dried in a dessicator over phosphorous pentoxide to give 13 g (49%) of 1-(1H-indol-3-yl)-2-(2-methoxyphenyl)ethanone 3 as a cream solid.

Example 3

Preparation of 2-(2-methoxyphenyl)-1-(1-pentyl-1H-indol-3-yl)ethanone (JWH-250) 4

60% Sodium hydride in mineral oil (1.8 g, 45.23 mmol) was suspended in dimethylformamide (100 ml) and 1-(1H-indol-3-yl)-2-(2-methoxyphenyl)ethanone 3 (10 g, 37.70 mmol) was added portionwise at room temperature, allowing to stir further 45 min at room temperature after the addition was finished. 1-Bromopentane (7.02 ml, 56.55 mmol) was added dropwise at room temperature and the reaction mixture was stirred at room temperature overnight. Water (200 ml) was added and the mixture was extracted three times with ethyl acetate (3×200 ml). The organic fractions were combined, washed with water (200 ml) and brine (200 ml) and dried over sodium sulphate and concentrated in vacuo. The residue was purified by column chromatography (Biotage Isolera 4, SNAP-100 g, 5%-20% ethyl acetate hexane containing 5% dichloromethane) to give 6.2 g (41%) of 2-(2-methoxyphenyl)-1-(1-pentyl-1H-indol-3-yl)ethanone (JWH-250) 4 as an orange/tan solid.

Example 4

Preparation of 2-(2-hydroxyphenyl)-1-(1-pentyl-1H-indol-3-yl)ethanone (O-desmethyl JWH-250) 5

2-(2-Methoxyphenyl)-1-(1-pentyl-1H-indol-3-yl)ethanone (JWH-250) 4 (3 g, 8.94 mmol) was dissolved in anhydrous dichloromethane (40 ml) and cooled at −78° C. A solution of 1NBBr$_3$ (9.83 ml, 9.83 mmol) was added drop-wise and once the addition was complete the reaction mixture was allowed to warm up to room temperature and was stirred at room temperature overnight. The reaction mixture was poured into a solution of 2NHCl (100 ml) and stirred for 30 min, then extracted three times with dichloromethane (3×150 ml) and the combined organic fractions dried over sodium sulphate and concentrated in vacuo. The residue was purified by column chromatography (Biotage Isolera 4, SNAP-50 g, 0%-20% ethyl acetate in hexane) to give 840 mg (29%) of 2-(2-hydroxyphenyl)-1-(1-pentyl-1H-indol-3-yl)ethanone (O-desmethyl JWH-250) 5 as a solid.

Example 5

Preparation of t-Butyl 2-(2-(2-oxo-2-(1-pentyl-1H-indol-3-yl)ethyl)phenoxy)acetate (O-desmethyl JWH-250 t-Butyl 2-Carboxymethylether) 6

2-(2-hydroxyphenyl)-1-(1-pentyl-1H-indol-3-yl)ethanone (O-desmethyl JWH-250) 5 (840 mg, 2.61 mmol) was dissolved in acetonitrile (20 ml) followed by the addition of potassium carbonate (1.08 g, 7.83 mmol) and t-butyl bromoacetate (0.76 g, 3.91 mmol). The reaction mixture was heated at reflux overnight. The reaction mixture was filtered and the filtrate was concentrated in vacuo. The residue was purified by column chromatography (Biotage Isolera 4, SNAP-25 g, 0%-10% ethyl acetate in hexane) to give 1.09 g (96%) of t-butyl 2-(2-(2-oxo-2-(1-pentyl-1H-indol-3-yl)ethyl)phenoxy)acetate (O-desmethyl JWH-250 t-Butyl 2-CME) 6.

Example 6

Preparation of O-Desmethyl JWH-250 2-Carboxymethylether (Hapten 1)

t-Butyl 2-(2-(2-oxo-2-(1-pentyl-1H-indol-3-yl)ethyl)phenoxy)acetate (O-desmethyl JWH-250 t-butyl 2-CME) 6 (1.09 g, 2.50 mmol) was dissolved in dichloromethane (20 ml) and trifluoroacetic acid (10 ml) was added and the reaction mixture was stirred at room temperature overnight. The solvent was removed in vacuo and the residue was purified by column chromatography (Biotage Isolera 4, SNAP-50 g, 50% ethyl acetate in hexane) to give 512 mg (54%) of O-desmethyl JWH-250 2-CME (Hapten 1) as a tan solid.

Example 7

Conjugation of Hapten 1 to BSA

To a solution of (Hapten 1) (42.87 mg, 0.113 mM) in DMF (1.0 ml) was added N, N-dicyclohexylcarbodiimide (DCC) (25.64 mg, 0.13 mM) and N-hydroxysuccinimide (14.3 mg, 0.13 mM) and the mixture was stirred at room temperature overnight. The dicyclohexylurea formed was removed by filtration and the solution was added drop-wise to a solution of BSA (150 mg, 2.3 μM) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give Hapten-1-BSA.

MALDI results showed 31.93 molecules of hapten 1 had been conjugated to one molecule of BSA.

Example 8

Conjugation of (Hapten 1) to BTG (Immunogen-III)

To a solution of (Hapten 1) (51.33 mg, 0.14 mM) in DMF (1.0 ml) was added N, N-dicyclohexylcarbodiimide (DCC) (30.74 mg, 0.15 mM) and N-hydroxysuccinimide (17.13 mg, 0.15 mM) and the mixture was stirred at room temperature overnight. The dicyclohexylurea formed was removed by filtration and the solution was added drop wise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give immunogen-III

Example 9

Conjugation of (Hapten 1) to HRP

EDC hydrochloride (10 mg) was dissolved in water (0.5 ml) and immediately added to a solution of (Hapten-1) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Example 10

Preparation of ethyl 5-(3-(2-(2-methoxyphenyl) acetyl)-1H-indol-1-yl)pentanoate (Ethyl N-(carboxybutyrate) JWH-250) 7

60% Sodium hydride in mineral oil (480 mg, 12 mmol) was suspended in dimethylformamide (50 ml) and 1-(1H- indol-3-yl)-2-(2-methoxyphenyl)ethanone 3 (2.66 g, 10 mmol) was added portionwise at room temperature, allowing to stir further 45 min at room temperature after the addition was finished. Ethyl 5-bromovalerate (2.37 ml, 15 mmol) was added dropwise at room temperature and the reaction mixture was stirred at room temperature overnight. The solvents were removed in vacuo and the residue was taken into water (30 ml) and extracted three times with ethyl acetate (3×50 ml). The organic fractions were combined and dried over sodium sulphate and concentrated in vacuo. The residue was purified by column chromatography (silica gel, 20% ethyl acetate in hexane) to give 856 mg (22%) of ethyl 5-(3-(2-(2-methoxyphenyl)acetyl)-1H-indol-1-yl)pentanoate (Ethyl N-(carboxybutyrate) JWH-250) 7 as a semi solid.

Example 11

Preparation of 5-(3-(2-(2-methoxyphenyl)acetyl)-1H-indol-1-yl)pentanoic acid [N-(carboxybutyric acid) JWH-250] (Hapten 2)

Ethyl 5-(3-(2-(2-methoxyphenyl)acetyl)-1H-indol-1-yl) pentanoate [Ethyl N-(carboxybutyrate) JWH-250] 7 (856 mg, 2.18 mmol) was dissolved in tertahydrofuran (15 ml) and water (15 ml) was added followed by potassium hydroxide (287 mg, 4.36 mmol). The reaction mixture was stirred at room temperature overnight. The solvent was removed in vacuo, the residue was acidified to pH 3 and extracted three times with ethyl acetate (3×50 ml). The organic fractions were combined, dried over sodium sulphate and concentrated under vacuo. The residue was purified by column chromatography (silica gel, 50%-100% ethyl acetate in hexane) and then recrystalised from ethylacetate/hexane to give 565 mg (71%) 5-(3-(2-(2-methoxyphenyl)acetyl)-1H-indol-1-yl)pentanoic acid [N-(carboxybutyric acid) JWH-250] (Hapten 2) as a white solid.

Example 12

Conjugation of [N-(carboxybutyric acid) JWH-250] (Hapten-2) to BSA

To a solution of [N-(carboxybutyric acid) JWH-250] (Hapten-2) (41.29 mg, 0.113 mM) in DMF (1.0 ml) was added N, N-dicyclohexylcarbodiimide (DCC) (25.64 mg, 0.13 mM) and N-hydroxysuccinimide (14.3 mg, 0.13 mM) and the mixture was stirred at room temperature overnight. The dicyclohexylurea formed was removed by filtration and the solution was added drop-wise to a solution of BSA (150 mg, 2.3 µM) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give [N-(carboxybutyric acid) JWH-250]-BSA.

MALDI results showed 26.86 molecules of hapten-2 had been conjugated to one molecule of BSA.

Example 13

Conjugation of [N-(carboxybutyric acid) JWH-250] (Hapten-2) to BTG (Immunogen-V)

To a solution of [N-(carboxybutyric acid) JWH-250] (Hapten-2) (49.44 mg, 0.14 mM) in DMF (1.0 ml) was added N, N-dicyclohexylcarbodiimide (DCC) (30.7 mg, 0.15 mM) and N-hydroxysuccinimide (17.12 mg, 0.15 mM) and the mixture was stirred at room temperature overnight. The dicyclohexylurea formed was removed by filtration and the solution was added drop wise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give immunogen-V.

Example 14

Conjugation of [N-(carboxybutyric acid) JWH-250] (Hapten-2) to HRP

EDC hydrochloride (10 mg) was dissolved in water (0.5 ml) and immediately added to a solution of [N-(carboxybutyric acid) JWH-250] (Hapten-2) (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The hapten-HRP conjugate was then dialysed overnight against 10 L of PBS at pH 7.2 at 4° C.

Immunogen Prepared from Hapten of FIG. 7

Example 15

Preparation of (2-methyl-1H-indol-3-yl)(naphthalen-1-yl) methanone 2

2-Methylindole 1 (10 g, 76.3 mmol) was dissolved in diethylether (100 ml) under nitrogen atmosphere and cooled to 0° C. MeMgBr (3M) solution (26.7 ml, 80.15 mmol) was added dropwise and allowed to stir at room temperature for 3 hours. In the meantime, 1-naphthoic acid (13.13 g, 76.3 mmol) was dissolved in thionyl chloride (50 ml) and refluxed for 90 min, then the solvent was removed under vacuo and the residue was dissolved in diethylether (50 ml). The resulting solution was added dropwise to the indole reaction mixture at 0° C. and then allowed to stir at room temperature for 2 hours. A solution of ammonium chloride (200 ml) was added to the reaction mixture and the resulting mixture was stirred at room temperature overnight. The solid that was formed was collected by filtration, washed with water and hexane then dried in a dessicator over phosphorous pentoxide to give 9.7 g (45%) (2-methyl-1H-indol-3-yl)(naphthalen-1-yl) methanone 2 as a cream solid.

Example 16

Preparation of ethyl 4-(3-(1-naphthoyl)-2-methyl-1H-indol-1-yl) butanoate 3

60% Sodium hydride in mineral oil (266 mg, 6.65 mmol) was suspended in dimethylformamide (15 ml) and (2-Methyl-1H-indol-3-yl)(naphthalen-1-yl) methanone 2 (1.5 g, 5.54 mmol) was added portionwise at room temperature, allowing to stir further 30 min at room temperature after the addition was finished. Ethyl-4-bromoacetate (1.2 ml, 8.31 mmol) was added dropwise at room temperature and the reaction mixture was stirred at room temperature overnight. Solvents were removed in vacuo and the residue was partitioned between ethyl acetate (200 ml) and water (150 ml). The layers were separated and aqueous layer was extracted 2 times with ethyl acetate (2×100 ml). All the organic fractions were combined, dried over sodium sulphate and concentrated in vacuo. The residue was purified by column chromatography (silica gel, 20% ethyl acetate in hexane) to give 500 mg (23%) of ethyl 4-(3-(1-naphthoyl)-2-methyl-1H-indol-1-yl) butanoate 3 as semi-solid.

Example 17

Preparation of 4-(3-(1-naphthoyl)-2-methyl-1H-indol-1-yl)butanoic acid

Ethyl 4-(3-(1-naphthoyl)-2-methyl-1H-indol-1-yl) butanoate 3 (500 mg, 1.25 mmol) was dissolved in tertahydrofuran (5 ml) and water (5 ml) was added followed by potassium hydroxide (206 mg, 3.68 mmol). The reaction mixture was stirred at room temperature overnight. The solvent was removed in vacuo, the residue was acidified to pH3 and extracted three times with a mixture 1:1 ethyl acetate:tetrahydrofuran (3×50 ml). The organic fractions were combined, dried over sodium sulphate and concentrated under vacuo. The residue was purified by column chromatography (silica gel, ethyl acetate) to give 350 mg (75%) 4-(3-(1-naphthoyl)-2-methyl-1H-indol-1-yl)butanoic acid as a yellow solid.

Example 18

Conjugation of 4-(3-(1-naphthoyl)-2-methyl-1H-indol-1-yl) butanoic acid to BSA

To a solution of 4-(3-(1-naphthoyl)-2-methyl-1H-indol-1-yl) butanoic acid (41.97 mg, 0.09 mM) in DMF (1.0 ml) was added N, N-dicyclohexylcarbodiimide (DCC) (28.64 mg, 0.12 mM) and N-hydroxysuccinimide (14.3 mg, 0.12 mM) and the mixture was stirred at room temperature overnight. The dicyclohexylurea formed was removed by filtration and the solution was added drop-wise to a solution of BSA (150 mg, 2.3 µM) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give the conjugated molecule.

MALDI results showed 37.64 molecules of 4-(3-(1-naphthoyl)-2-methyl-1H-indol-1-yl) butanoic acid had been conjugated to one molecule of BSA.

Example 19

Conjugation of 4-(3-(1-naphthoyl)-2-methyl-1H-indol-1-yl) butanoic acid to BTG

To a solution of 4-(3-(1-naphthoyl)-2-methyl-1H-indol-1-yl) butanoic acid (50.25 mg, 0.14 mM) in DMF (1.0 ml) was added N, N-dicyclohexylcarbodiimide (DCC) (30.72 mg, 0.15 mM) and N-hydroxysuccinimide (17.13 mg, 0.15 mM) and the mixture was stirred at room temperature overnight. The dicyclohexylurea formed was removed by filtration and the solution was added drop wise to a solution of BTG (150 mg) in 50 mM sodium bicarbonate solution (pH 8.5) (10 ml). The mixture was then stirred overnight at 4° C. The solution was then dialysed against 50 mM phosphate buffer pH 7.2 (3 changes) for 24 hours at 4° C., and freeze-dried to give 4-(3-(1-naphthoyl)-2-methyl-1H-indol-1-yl) butanoic acid conjugated to BTG.

Example 20

Conjugation of 4-(3-(1-naphthoyl)-2-methyl-1H-indol-1-yl) butanoic acid to HRP

EDC hydrochloride (10 mg) was dissolved in water (0.5 ml) and immediately added to a solution of 4-(3-(1-naphthoyl)-2-methyl-1H-indol-1-yl) butanoic acid (2 mg) in DMF (0.2 ml). After mixing, this solution was added drop wise to a solution of HRP (20 mg) in water (1 ml). Sulfo-NHS (5 mg) was added and the reaction mixture was incubated in the dark at room temperature overnight. Excess hapten was removed with double PD-10 columns (Pharmacia) in series, pre-equilibrated with PBS at pH 7.2. The 4-(3-(1-naphthoyl)-2-methyl-1H-indol-1-yl) butanoic acid-HRP conjugate was then dialysed overnight against 10 L of PBS at pH 7.2 at 4° C.

Preparation of Antisera

In order to generate polyclonal antisera, each immunogen of the present invention is mixed with Freund's Adjuvant and the mixture is injected into a host animal, such as rabbit, sheep, mouse, guinea pig or horse. Sheep is the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

The specific antibodies prepared in this invention are useful as reagents in immunoassays for the detection or determination of synthetic cannabinoids and their metabolites in biological fluids.

Example 21

Preparation of Antibodies to Immunogens III, V and VI

General Method:

An aqueous solution of each immunogen was formulated with Freund's Complete Adjuvant (FCA) to form an emulsion consisting of 2 mg/ml* immunogen in 50% (v/v) FCA. Three sheep were immunised with this emulsion (1° immunisation), 0.25 ml being intramuscularly injected at each of four sites in the flank of each animal. Subsequent immunizations (boosts) contained 1 mg/ml* immunogen. All boosts were emulsified in 50% (v/v) Freund's Incomplete Adjuvant (FIA) and were administered in the same manner as the 1° immunisation, at monthly intervals. Blood sampling took place 7 to 14 days after each boost.

*The general procedure for immunogen administration is outlined above, however, it was necessary to deviate from this protocol in some cases, due to reduced immunogen concentrations (Immunogens II, III, IV, VII & VIII) and/or amount available (Immunogen VIII). Any deviations from the protocol described are outlined in Table 1 below and highlighted in bold.

TABLE 1

Amount and volume of immunogens administered for primary and subsequent boosts

| Immunogen | Primary Amount/ Volume | Boost Amount/ Volume |
|---|---|---|
| III | 2 mg/1.5 ml | 1 mg/1 ml |
| V | 2 mg/1 ml | 1 mg/1 ml |
| VI | 2 mg/1 ml | 1 mg/1 ml |

Blood Collection

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Processing & Extraction of Immunoglobulin (Ig) Fraction:

Samples are centrifuged at 4000 g for 30 minutes at 4° C. The serum is then poured off and centrifuged again at 16,000 g for 15 minutes at 4° C., before being aliquoted and stored at <−20° C.

Precipitation of IgG from polyclonal antisera is carried out in two steps, using caprylic acid initially to precipitate most of the non-Ig G proteins, including albumin, followed by ammonium sulphate to extract IgG from the supernatant. This method produces a highly purified IgG fraction.

8 ml of 60 mM sodium acetate buffer, pH 4.4 is added to 2 ml of antisera, followed by the addition of 200 µl of caprylic acid. The resulting mixture is mixed on a roller for 30 minutes at room temperature. The precipitate is removed by centrifuging the samples at 1000 g for 20 minutes at 4° C. and filtering the supernatant through a 0.2 µm Acrodisc™ filter. 1.4 ml of 0.5M carbonate-bicarbonate buffer, pH 10.7, is added to each sample supernatant and cooled to 4° C. 9 ml of saturated ammonium sulphate solution is added slowly whilst shaking and the resulting mixture is placed on a roller for 30 minutes at room temperature. The precipitate is extracted by centrifuging the samples at 1000 g for 35 minutes at 4° C. The supernatant is poured off and the pellet re-suspended in 2 ml PBS, pH 7.2. The sample is dialysed overnight at 4° C. in PBS, pH7.2 containing 0.09% azide. After dialysis, the sample is filtered using a 0.2 µm Acrodisc™ filter and aliquoted for storage at <20° C. The IgG fraction can then be evaluated by competitive ELISA microtiter plate assay, as described below.

Example 22

Characterisation of Antibodies to Immunogens III, V and VI

Standard Curves
General Method: Immunogen VI

Figure 1:
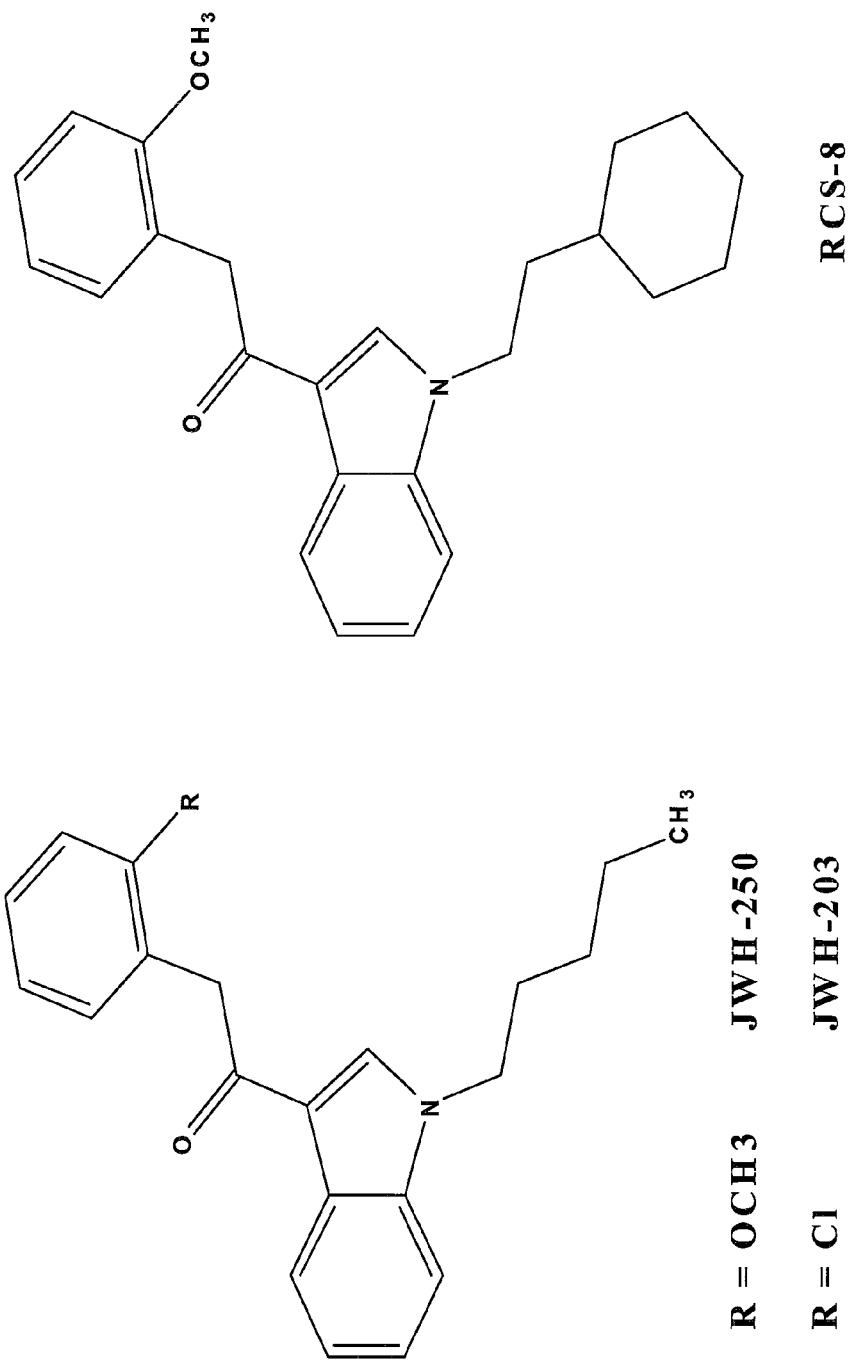
FIG. 1 contains diagrams of chemical structures of JWH-250, JWH-203, JWH-251 and RCS-8.
Figure 2:
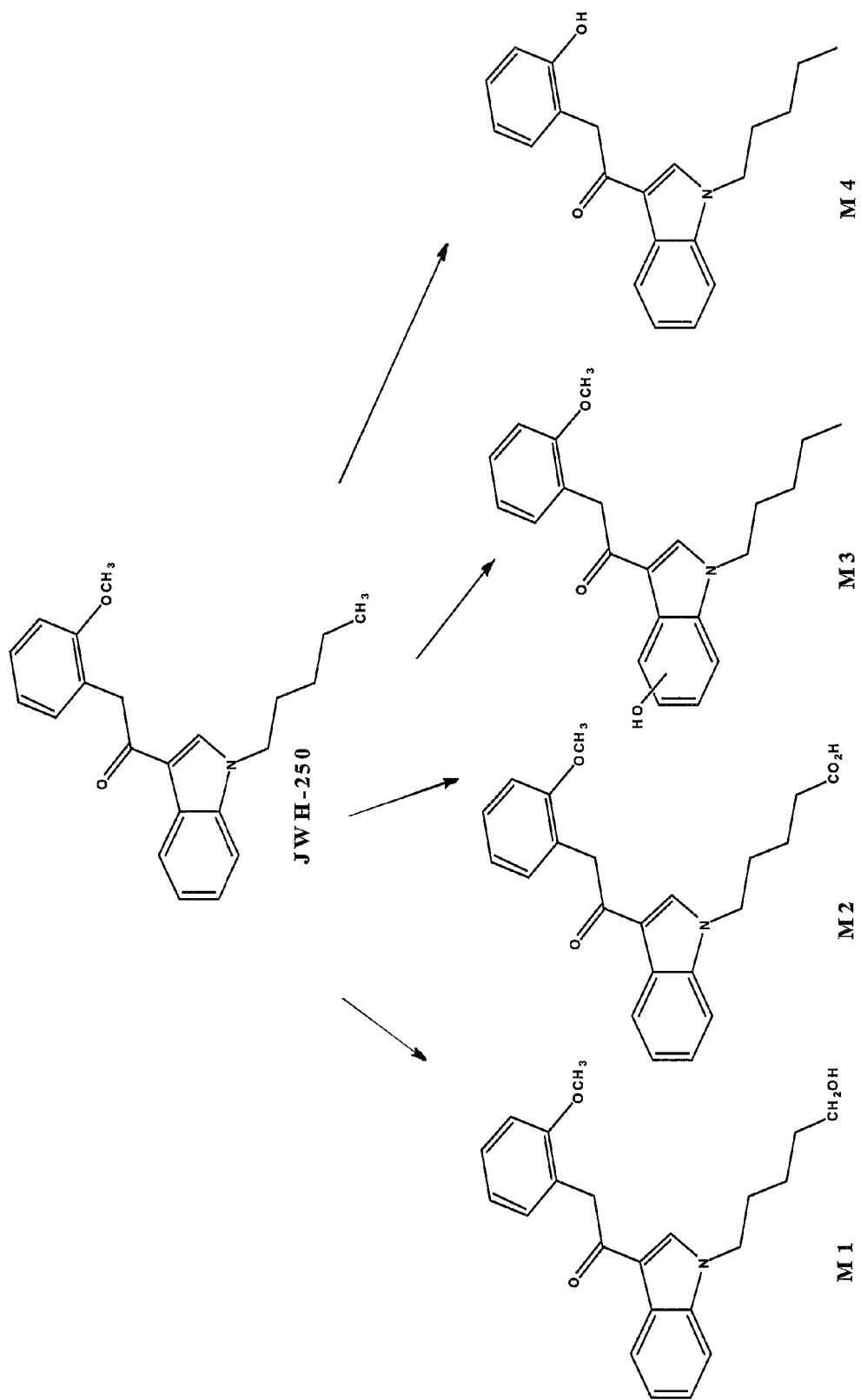
FIG. 2 contains diagrams of chemical structures of JWH-250 Main Metabolites.
Figure 3:
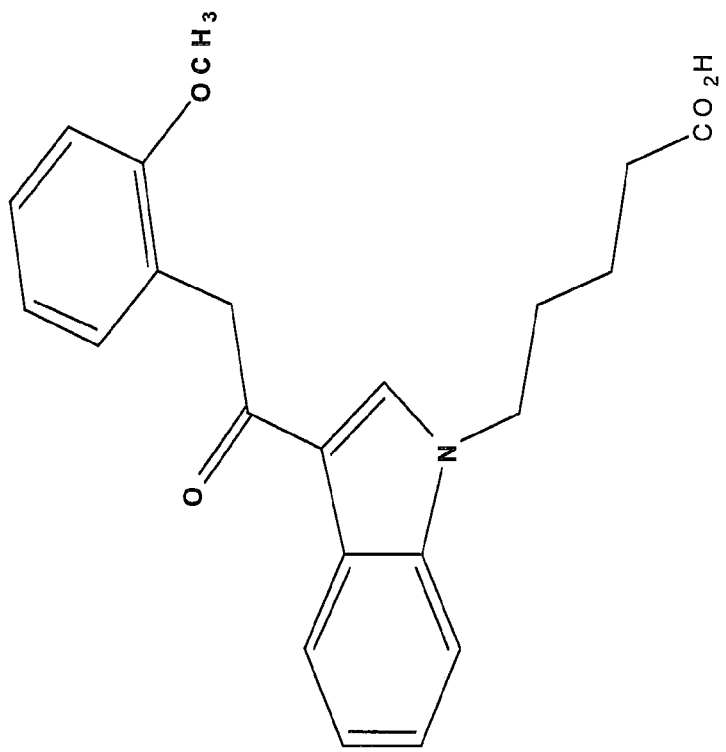
FIG. 3 contains diagrams of chemical structures of Hapten-1 and Hapten-2—used to prepare Immunogens III and V, respectively.
Figure 3:
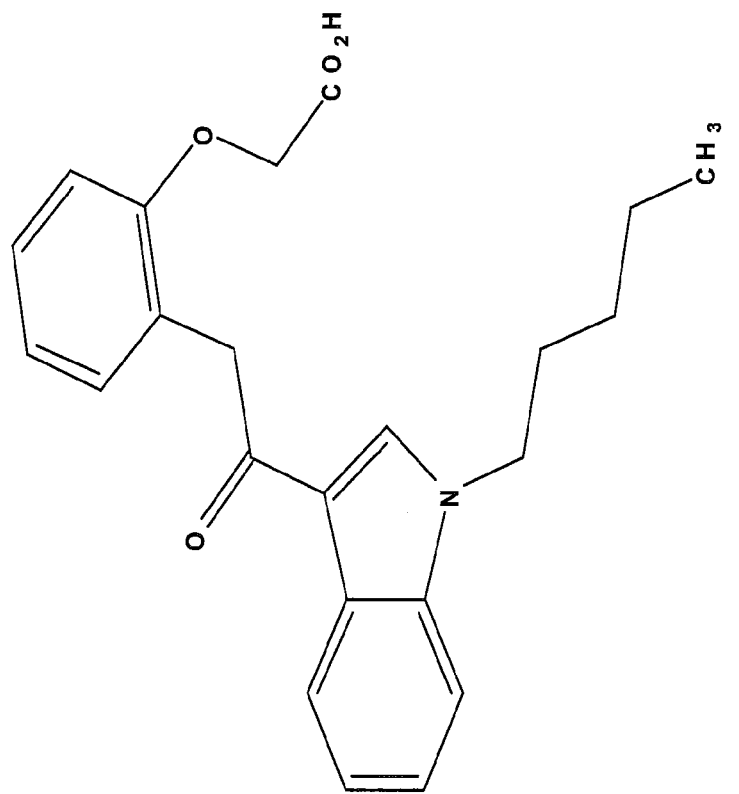

The wells of an enhanced binding 96 well polystyrene microtiter plate were coated with IgG fraction of antiserum raised to Immunogen VI, diluted in 10 mM Tris, pH8.5 (125 µl/well). The appropriate antibody coating dilution was determined using standard ELISA checkerboard techniques. The plate was incubated overnight at 4° C., washed 4 times over 10 minutes with Tris buffered saline containing Tween 20 (TBST) and tapped dry. Standard solutions of RCS-4 were prepared in TBST at 0, 0.3125, 0.625, 1.25, 2.5, 5, 10 and 20 ng/ml, and 50 µl of each was added to the appropriate wells (see FIG. 1). 75 µl of conjugate (appropriate hapten-HRP) diluted in Tris buffer (pH 7.2) containing EDTA, D-mannitol, sucrose, thimerosal and BSA, was added to each of the wells. The appropriate dilution of conjugate was also determined using standard ELISA checkerboard techniques. The plate was incubated at 25° C. for 1 hour. Excess unbound conjugate was removed by washing 6 times over a 10 minute period with TBST. 125 µl of tetramethylbenzidine (TMB) substrate solution was added to each well of the plate that was then incubated for 20 minutes in the dark at room temperature. The reaction was terminated by addition of 125 µl 0.2M $H_2SO_4$ to each well. The absorbance was then measured at 450 nm using a microtiter plate reader. The data are inputted to a computer program called 'KC Junior'. It is a 4 parameter fit curve and allow the calculation of concentrations between the standard runs. This program is used to calculate the IC50s by dividing the 0 ng/ml OD value by 2 and obtaining the concentration value from the curve for this OD. The data generated in the assay and inputted to a computer program called 'KC Junior' are presented in Table 3.

General Method: Immunogen III

In a similar manner to that described above, the wells of a 96-well microtiter plate were coated with the IgG fraction of the antiserum raised to Immunogen III. Standard solutions (JWH-250 for Immunogen III) were applied at 0, 0.625, 1.25, 2.5, 5, 10, 20 and 40 ng/ml and conjugate was employed as detection reagent. The data generated are presented in Table 3.

General Method: Immunogen V

In a similar manner to that described above, the wells of a 96-well microtiter plate were coated with the IgG fraction of the antiserum raised to Immunogen V. Standard solutions (RCS-8 for Immunogen V) were prepared in TBST at 0, 1.25, 2.5, 5, 10, 20, 40 and 80 ng/ml and conjugate was employed as detection reagent. The data generated are presented in Table 3.

The data set out in Tables 3 and 4 are generated using antibodies raised against the indicated Immunogens in a competitive binding assay with the indicated tracers, using the indicated standards:

TABLE 2

| | Immunogen/ Hapten | Antibody | Standard | Tracer/ hapten |
|---|---|---|---|---|
| Immunogen 3 | CJ-6-148/LK1108 | RS2133B4 | JWH-250 | ESC6049/ LK1111 |
| Immunogen 5 | CJ-7-121/LK1162 | RS2199B3 | RCS-8 | ESC6557/ LK1182 |
| Immunogen 6 | CJ-7-141/LK1161 | RS2245B3 | RCS-4 | ESC6585/ LK1188 |

The tracers are illustrated in FIG. 10 and the Immunogens are illustrated in FIG. 11.

TABLE 3

Data generated from competitive microtiter plate assays for Synthetic Cannabinoids and their metabolites, employing antisera generated to Immunogens I-VIII Table 3a

| JWH-250 ng/ml | Antibody to Immunogen 3 | |
|---|---|---|
| | A450 | % B/B$_0$ |
| 0 | 1.844 | 100 |
| 1 | 1.557 | 84 |
| 1 | 1.287 | 70 |
| 3 | 1.0925 | 59 |
| 5 | 0.796 | 43 |
| 10 | 0.6905 | 38 |
| 20 | 0.5415 | 29 |
| 40 | 0.4165 | 23 |
| IC50 (ng/ml) | 3.850 | |

TABLE 3-continued

Data generated from competitive microtiter plate assays for Synthetic Cannabinoids and their metabolites, employing antisera generated to Immunogens I-VIII Table 3b

| RCS-8 | Antibody to Immunogen 5 | | RCS-4 | Antibody to Immunogen 6 | |
|---|---|---|---|---|---|
| ng/ml | A450 | % B/B$_0$ | ng/ml | A450 | % B/B$_0$ |
| 0 | 1.61 | 100 | 0 | 1.774 | 100 |
| 1.25 | 1.319 | 82 | 0.3125 | 1.305 | 74 |
| 2.5 | 1.147 | 71 | 0.625 | 1.066 | 60 |
| 5 | 0.916 | 57 | 1.25 | 0.814 | 46 |
| 10 | 0.689 | 43 | 2.5 | 0.606 | 34 |
| 20 | 0.551 | 34 | 5 | 0.452 | 25 |
| 40 | 0.403 | 25 | 10 | 0.321 | 18 |
| 80 | 0.298 | 19 | 20 | 0.228 | 13 |
| IC50 (ng/ml) | 7.23 | | IC50 (ng/ml) | 1.020 | |

$A_{450}$ = absorbance at 450 nm
B = absorbance at 450 nm at xng/ml standard concentration
B$_0$ = absorbance at 450 nm at 0 ng/ml standard concentration
IC$_{50}$ = standard concentration which produces 50% B/B$_0$ Cross Reactivity In order to determine the specificity of the competitive ELISAs, standard solutions of a range of structurally similar synthetic cannabinoids and their metabolites were prepared in TBST. Using the calibration curves generated and employing a single level of cross reactants, these were used to determine the cross-reactivity of each immunoassay with these substances. The results of this study are presented in Table 4, as % B/B$_0$.

TABLE 4

Cross reactivity of the competitive ELISAs for synthetic cannabinoids and their metabolites

| | Cross-reactants at 100 ng/ml; 1000 ng/ml | Antibody to Immunogen III % B/B0 | Antibody to Immunogen V % B/B0 | Antibody to Immunogen VI % B/B0 |
|---|---|---|---|---|
| 1 | JWH-018 | 78.39 | 78.01 | 82.47 |
| 2 | 2-OH JWH-018 (JWH-018 2-hydroxyindole metabolite) | 97.61 | 98.82 | 101.92 |
| 3 | 4-OH JWH-018 (JWH-018 4-hydroxyindole metabolite) | 82.22 | 83.42 | 92.00 |
| 4 | 5-OH JWH-018 (JWH-018 5-hydroxyindole metabolite) | 96.24 | 88.70 | 95.94 |
| 5 | 6-OH JWH-018 (JWH-018 6-hydroxyindole metabolite) | 92.91 | 75.65 | 91.26 |
| 6 | 7-OH JWH-018 (JWH-018 7-hydroxyindole metabolite) | 97.89 | 80.99 | 91.71 |
| 7 | N-desalkyl JWH-018: LK1012 10CD194 | 99.73 | 81.80 | 87.49 |
| 8 | (±)-JWH 018 N-(4-hydroxypentyl) metabolite | 86.69 | 75.59 | 76.16 |
| 9 | JWH-018 N-(5-hydroxypentyl) metabolite | 89.74 | 70.25 | 61.67 |
| 10 | JWH-018 N-pentanoic acid metabolite | 100.98 | 72.42 | 65.90 |
| 11 | JWH 018 N-(1,2-dimethylpropyl) isomer | 90.17 | 74.41 | 83.71 |
| 12 | JWH 018 2'-naphthyl isomer | 76.35 | 88.32 | 44.48 |
| 13 | JWH 018 adamantyl analog | 84.69 | 86.65 | 93.91 |
| 14 | JWH-018 N-(1-methylbutyl) isomer | 87.31 | 76.65 | 85.57 |
| 15 | JWH-018 N-(2,2-dimethylpropyl) isomer | 95.58 | 67.14 | 78.92 |
| 16 | JWH-018 6-methoxyindole analogue | 85.67 | 73.60 | 86.92 |
| 17 | JWH-018 N-(2-methylbutyl) isomer (JWH-073 2-methylbutyl homologue) | 92.91 | 69.13 | 80.10 |
| 18 | JWH 018 N-(3-methylbutyl) isomer (JWH-073 3-methylbutyl homologue) | 82.58 | 63.42 | 66.63 |
| 19 | JWH-073 | 81.25 | 66.65 | 74.80 |
| 20 | 2-OH JWH-073 (JWH-073 2-hydroxyindole metabolite) | 97.53 | 91.80 | 89.23 |

TABLE 4-continued

Cross reactivity of the competitive ELISAs for synthetic cannabinoids and their metabolites

| | Cross-reactants at 100 ng/ml; 1000 ng/ml | Antibody to Immunogen III % B/B0 | Antibody to Immunogen V % B/B0 | Antibody to Immunogen VI % B/B0 |
|---|---|---|---|---|
| 21 | 4-OH JWH-073 (JWH-073 4-hydroxyindole metabolite) | 84.57 | 76.09 | 84.39 |
| 22 | 5-OH JWH-073 (JWH-073 5-hydroxyindole metabolite) | 95.65 | 82.86 | 85.96 |
| 23 | 6-OH JWH-073 (JWH-073 6-hydroxyindole metabolite) | 94.60 | 68.70 | 84.50 |
| 24 | 7-OH JWH-073 (JWH-073 7-hydroxyindole metabolite) | 95.81 | 73.04 | 81.62 |
| 25 | JWH-073 N-(3-hydroxybutyl) metabolite | 94.05 | 63.79 | 72.55 |
| 26 | JWH-073 N-(4-hydroxybutyl) metabolite | 87.63 | 63.73 | 70.57 |
| 27 | JWH-073 N-butanoic acid metabolite | 97.45 | 70.75 | 76.27 |
| 28 | JWH 073 2-methylnaphthyl analog | 86.14 | 77.45 | 86.98 |
| 29 | JWH-073 4-methylnaphthyl analogue | 78.03 | 65.84 | 70.97 |
| 30 | JWH-007 | 81.87 | 75.22 | 81.74 |
| 31 | JWH-011 | 93.19 | 83.73 | 88.22 |
| 32 | JWH-015 | 93.97 | 73.42 | 77.06 |
| 33 | JWH-016 | 82.93 | 69.38 | 80.10 |
| 34 | JWH-019 | 88.06 | 70.25 | 78.02 |
| 35 | JWH 019 5-hydroxyindole metabolite (JWH-019-M2) | 95.38 | 79.13 | 89.29 |
| 36 | JWH-020 | 93.85 | 71.43 | 82.41 |
| 37 | JWH-022 | 76.82 | 61.86 | 75.42 |
| 38 | JWH-030 | 95.34 | 77.27 | 86.70 |
| 39 | JWH-081 | 73.73 | 69.32 | 70.63 |
| 40 | JWH-081 2-methoxynaphthyl isomer or (JWH-267) | 85.59 | 70.37 | 86.87 |
| 41 | JWH-081 5-methoxynaphthyl isomer | 76.35 | 90.40 | 77.74 |
| 42 | JWH-081 7-methoxynaphthyl isomer (JWH-164) | 75.18 | 87.25 | 92.27 |
| 43 | JWH-081 N-(5-hydroxypentyl) metabolite | 76.44 | 72.78 | 69.47 |
| 44 | JWH-098 | 74.71 | 81.09 | 78.96 |
| 45 | JWH-122 | 69.90 | 69.63 | 75.29 |
| 46 | JWH 122 6-methylnaphthyl isomer | 73.75 | 77.08 | 84.77 |
| 47 | JWH 122 7-methylnaphthyl isomer | 71.72 | 78.80 | 86.92 |
| 48 | JWH 122 2-methylnaphthyl isomer | 80.25 | 83.38 | 90.59 |
| 49 | JWH-122 N-(5-hydroxypentyl) metabolite | 81.72 | 68.77 | 71.84 |
| 50 | JWH-133 | 97.40 | 90.40 | 93.73 |
| 51 | JWH-147 | 93.37 | 83.09 | 93.42 |
| 52 | JWH-164 (JWH-081 7-methoxynaphthyl isomer) | 72.63 | 82.81 | 89.29 |
| 53 | JWH-182 | 76.14 | 82.38 | 85.69 |
| 55 | JWH-200 4-hydroxyindole metabolite | 95.93 | 74.79 | 90.44 |
| 56 | JWH-200 5-hydroxyindole metabolite | 96.49 | 82.38 | 93.65 |
| 57 | JWH-200 6-hydroxyindole metabolite | 95.45 | 69.91 | 88.68 |
| 58 | JWH-200 2'-naphthyl isomer | 99.13 | 75.36 | 20.66 |
| 59 | JWH-201 | 27.93 | 68.62 | 69.32 |
| 60 | JWH-203 | 18.15 | 15.33 | 83.09 |
| 61 | JWH 203 3-chloro isomer (JWH-237) | 22.69 | 27.22 | 72.53 |
| 62 | JWH-206 (JWH-203 4-chloro isomer) | 26.33 | 51.00 | 78.35 |
| 63 | JWH-210 | 69.64 | 70.20 | 72.07 |
| 64 | JWH-210 2-ethylnaphthyl isomer | 85.02 | 85.10 | 89.90 |
| 65 | JWH-210 7-ethylnaphthyl isomer or JWH-234 | 73.32 | 85.10 | 87.07 |
| 66 | JWH-210 N-(5-carboxypentyl) metabolite | 94.24 | 70.77 | 63.50 |
| 67 | JWH-210 5-hydroxyindole metabolite | 87.01 | 79.94 | 86.92 |
| 68 | JWH-250 | 11.91 | 8.74 | 82.17 |
| 69 | JWH 250 N-(5-hydroxypentyl) metabolite | 48.72 | 6.88 | 78.58 |
| 70 | JWH 250 N-(5-carboxypentyl) metabolite | 89.61 | 8.60 | 85.31 |
| 71 | JWH 250 5-hydroxyindole metabolite | 65.83 | 37.39 | 91.28 |
| 72 | JWH-251 | 17.28 | 13.61 | 79.72 |
| 73 | JWH 251 3-methylphenyl isomer | 21.39 | 26.65 | 73.53 |
| 74 | JWH-302 | 19.97 | 32.66 | 71.16 |
| 75 | JWH-398 | 71.37 | 65.76 | 72.30 |
| 76 | JWH-398 5-chloronaphthyl isomer | 64.92 | 70.34 | 76.13 |
| 77 | JWH-398 N-(5-hydroxypentyl) metabolite | 76.01 | 55.87 | 69.24 |

TABLE 4-continued

Cross reactivity of the competitive ELISAs for synthetic cannabinoids and their metabolites

| Cross-reactants at 100 ng/ml; 1000 ng/ml | Antibody to Immunogen III % B/B0 | Antibody to Immunogen V % B/B0 | Antibody to Immunogen VI % B/B0 |
|---|---|---|---|
| 78 AM-630 (other name 6-Iodopravadoline) | 91.34 | 71.78 | 39.25 |
| 79 AM-694 | 72.80 | 64.61 | 70.77 |
| 80 AM-694 3-iodo isomer | 67.86 | 63.18 | 44.38 |
| 81 AM-694 4-iodo isomer | 65.53 | 77.65 | 16.99 |
| 82 AM-1220 | 99.70 | 63.74 | 81.44 |
| 84 AM-1241 | 102.11 | 71.68 | 99.43 |
| 85 AM-2201 | 67.95 | 76.07 | 76.96 |
| 86 AM-2201 N-(4-fluoropentyl) isomer | 68.00 | 52.90 | 71.98 |
| 87 AM-2201 N-(4-hydroxypentyl) metabolite | 68.76 | 50.40 | 77.68 |
| 88 AM-2233 | 95.28 | 54.35 | 79.16 |
| 89 CP-49,497-C7 ((+−) CP 47,497) | 96.91 | 69.53 | 95.90 |
| 90 CP-47,497-para-quinone analogue | 96.58 | 72.98 | 94.38 |
| 91 CP-49,497-C8-homologue ((+− CP) 47,497-C8-homologue) | 95.39 | 86.41 | 100.84 |
| 92 ((+−)-CP 55,940) | 93.49 | 80.97 | 98.86 |
| 93 (−)-CP 55,940 | 90.16 | 91.41 | 94.76 |
| 94 (+)-CP 55,940 | 92.49 | 74.18 | 94.76 |
| 95 HU-210 | 91.13 | 67.43 | 90.89 |
| 96 HU-211 (Dexanabinol) | 95.96 | 71.68 | 98.97 |
| 97 HU-308 | 96.26 | 71.33 | 97.34 |
| 98 RCS-4 | 57.10 | 64.84 | 4.90 |
| 99 RCS-4 2-methoxy isomer | 64.43 | 68.38 | 81.06 |
| 100 RCS-4 3-methoxy isomer | 58.00 | 66.18 | 41.84 |
| 101 RCS-4-C4 homologue (BTM-4, SR-19, OBT-199, E-4) | 62.80 | 76.87 | 4.40 |
| 102 RCS-4 N-(4-hydroxypentyl) metabolite | 66.40 | 71.93 | 5.69 |
| 103 RCS-4 N-(5-hydroxypentyl) metabolite | 72.34 | 63.69 | 3.76 |
| 104 RCS-4 N-(5-carboxypentyl) metabolite | 91.87 | 60.79 | 4.25 |
| 105 RCS-8 (SR-18) | 64.72 | 8.34 | 85.46 |
| 106 RCS-8 3-methoxy isomer | 69.47 | 38.01 | 79.95 |
| 107 RCS-8 4-methoxy isomer | 76.06 | 81.97 | 89.48 |
| 108 (+)WIN 55212-2 (mesylate) | 93.28 | 68.43 | 91.65 |
| 109 Win 55,212-3 mesylate | 87.64 | 72.78 | 83.98 |
| 110 WIN-48,098 (other name Pravadoline) | 89.21 | 77.87 | 23.84 |
| 111 WIN 55,225 (other name JWH-200) | 88.39 | 49.45 | 71.03 |
| 112 Delta 9 THC | 91.21 | 65.28 | 94.84 |
| 113 Indole-3-carboxylic Acid | 91.19 | 64.69 | 95.41 |
| 114 Cannabinol | 97.02 | 64.54 | 95.90 |
| 115 5-hydroxyindole-3-acetic acid (5-HIAA) | 90.54 | 92.46 | 95.75 |
| 116 Serotonin HCl | 87.69 | 85.91 | 98.60 |
| 117 5-hydroxytryptophol | 85.39 | 90.61 | 95.67 |
| 118 (−)-11-nor-9-Carboxy-delta9-THC | 89.45 | 89.31 | 96.32 |

| Cross-Reactant | CAS Registry Number |
|---|---|
| JWH-018 | 209414-07-3 |
| 2-OH JWH-018 (JWH-018 2-hydroxyindole metabolite) | |
| 4-OH JWH-018 (JWH-018 4-hydroxyindole metabolite) | |
| 5-OH JWH-018 (JWH-018 5-hydroxyindole metabolite) | 335161-21-2 |
| 6-OH JWH-018 (JWH-018 6-hydroxyindole metabolite) | |
| 7-OH JWH-018 (JWH-018 7-hydroxyindole metabolite) | |
| N-desalkyl JWH-018: LK1012 10CD194 | |
| (±)-JWH 018 N-(4-hydroxypentyl) metabolite | |
| JWH-018 N-(5-hydroxypentyl) metabolite | |
| JWH-018 N-pentanoic acid metabolite | |
| JWH 018 N-(1,2-dimethylpropyl) isomer | |
| JWH 018 2'-naphthyl isomer | 1131605-25-8 |
| JWH 018 adamantyl analog | |
| JWH-018 N-(1-methylbutyl) isomer | |
| JWH-018 N-(2,2-dimethylpropyl) isomer | |
| JWH-018 6-methoxyindole analogue | |
| JWH-018 N-(2-methylbutyl) isomer (JWH-073 2-methylbutyl homologue) | |
| JWH 018 N-(3-methylbutyl) isomer (JWH-073 3-methylbutyl homologue) | |
| JWH-073 | 208987-48-8 |
| 2-OH JWH-073 (JWH-073 2-hydroxyindole metabolite) | |
| 4-OH JWH-073 (JWH-073 4-hydroxyindole metabolite) | |
| 5-OH JWH-073 (JWH-073 5-hydroxyindole metabolite) | |
| 6-OH JWH-073 (JWH-073 6-hydroxyindole metabolite) | |
| 7-OH JWH-073 (JWH-073 7-hydroxyindole metabolite) | |
| JWH-073 N-(3-hydroxybutyl) metabolite | |
| JWH-073 N-(4-hydroxybutyl) metabolite | |
| JWH-073 N-butanoic acid metabolite | |
| JWH 073 2-methylnaphthyl analog | |
| JWH-073 4-methylnaphthyl analogue | |
| JWH-007 | 155471-10-6 |
| JWH-011 | 155471-13-9 |
| JWH-015 | 155471-08-2 |
| JWH-016 | 155471-09-3 |
| JWH-019 | 209414-08-4 |
| JWH 019 5-hydroxyindole metabolite (JWH-019-M2) | |
| JWH-020 | 209414-09-5 |
| JWH-022 | 209414-16-4 |

-continued

| Cross-Reactant | CAS Registry Number |
|---|---|
| JWH-030 | 162934-73-8 |
| JWH-081 | 210179-46-7 |
| JWH-081 2-methoxynaphthyl isomer or (JWH-267) | 824960-76-1 |
| JWH-081 5-methoxynaphthyl isomer | |
| JWH-081 7-methoxynaphthyl isomer (JWH-164) | 824961-61-7 |
| JWH-081 N-(5-hydroxypentyl) metabolite | |
| JWH-098 | 316189-74-9 |
| JWH-122 | 619294-47-2 |
| JWH 122 6-methylnaphthyl isomer | |
| JWH 122 7-methylnaphthyl isomer | 824960-56-7 |
| JWH 122 2-methylnaphthyl isomer | |
| JWH-122 N-(5-hydroxypentyl) metabolite | |
| JWH-133 | 259869-55-1 |
| JWH-147 | 914458-20-1 |
| JWH-164 (JWH-081 7-methoxynaphthyl isomer) | 824961-61-7 |
| JWH-182 | 824960-02-3 |
| JWH-200 4-hydroxyindole metabolite | |
| JWH-200 5-hydroxyindole metabolite | |
| JWH-200 6-hydroxyindole metabolite | |
| JWH-200 2'-naphthyl isomer | 133438-66-1 |
| JWH-201 | 864445-47-6 |
| JWH-203 | 864445-54-5 |
| JWH 203 3-chloro isomer (JWH-237) | 864445-56-7 |
| JWH-206 (JWH-203 4-chloro isomer) | 864445-58-9 |
| JWH-210 | 824959-81-1 |
| JWH-210 2-ethylnaphthyl isomer | |
| JWH-210 7-ethylnaphthyl isomer or JWH-234 | 824960-64-7 |
| JWH-210 N-(5-carboxypentyl) metabolite | |
| JWH-210 5-hydroxyindole metabolite | |
| JWH-250 | 864445-43-2 |
| JWH 250 N-(5-hydroxypentyl) metabolite | |
| JWH 250 N-(5-carboxypentyl) metabolite | |
| JWH 250 5-hydroxyindole metabolite | |
| JWH-251 | 864445-39-6 |
| JWH 251 3-methylphenyl isomer | |
| JWH-302 | 864445-45-4 |
| JWH-398 | 1292765-18-4 |
| JWH-398 5-chloronaphthyl isomer | |
| JWH-398 N-(5-hydroxypentyl) metabolite | |
| AM-630 (other name 6-Iodopravadoline) | 164178-33-0 |
| AM-694 | 335161-03-0 |
| AM-694 3-iodo isomer | |
| AM-694 4-iodo isomer | |
| AM-1220 | 137642-54-7 |
| AM-1241 | 444912-48-5 |
| AM-2201 | 335161-24-5 |
| AM-2201 N-(4-fluoropentyl) isomer | |
| AM-2201 N-(4-hydroxypentyl) metabolite | |
| AM-2233 | 444912-75-8 |
| CP-49,497-C7 ((+−) CP 47,497) | |
| CP-47,497-para-quinone analogue | |
| CP-49,497-C8-homologue ((+− CP) 47,497-C8-homologue) | |
| ((+−)-CP 55,940) | |
| (−)-CP 55,940 | |
| (+)-CP 55,940 | |
| HU-210 | |
| HU-211 (Dexanabinol) | |
| HU-308 | |
| RCS-4 | 1345966-78-0 |
| RCS-4 2-methoxy isomer | |
| RCS-4 3-methoxy isomer | |
| RCS-4-C4 homologue (BTM-4, SR-19, OBT-199, E-4) | |
| RCS-4 N-(4-hydroxypentyl) metabolite | |
| RCS-4 N-(5-hydroxypentyl) metabolite | |
| RCS-4 N-(5-carboxypentyl) metabolite | |
| RCS-8 (SR-18) | 1345970-42-4 |
| RCS-8 3-methoxy isomer | |
| RCS-8 4-methoxy isomer | |
| (+)WIN 55212-2 (mesylate) | 131543-23-2 |
| Win 55,212-3 mesylate | 131543-25-4 |
| WIN-48,098 (other name Pravadoline) | 92623-83-1 |
| WIN 55,225 (other name JWH-200) | 103610-04-4 |
| Delta 9 THC | 1972-08-3 |

-continued

| Cross-Reactant | CAS Registry Number |
|---|---|
| Indole-3-carboxylic Acid | 87-51-4 |
| Cannabinol | 521-35-7 |
| 5-hydroxyindole-3-acetic acid (5-HIAA) | 54-16-0 |
| Serotonin HCl | 153-98-0 |
| 5-hydroxytryptophol | 154-02-9 |
| (−)-11-nor-9-Carboxy-delta9-THC | 56354-06-4 |

The standards used for the Table 2 $IC_{50}$ data generation are:

Immunogen III—JWH-250

Immunogen V—RCS-8

Immunogen VI—RCS-4

| | Immunogen/ Hapten | Antibody | Standard | Tracer/ hapten |
|---|---|---|---|---|
| Immunogen 3 | CJ-6-148/LK1108 | RS2133B4 | JWH-250 | ESC6049/ LK1111 |
| Immunogen 5 | CJ-7-121/LK1162 | RS2199B3 | RCS-8 | ESC6557/ LK1182 |
| Immunogen 6 | CJ-7-141/LK1161 | RS2245B3 | RCS-4 | ESC6585/ LK1188 |

The invention claimed is:

1. An antibody which binds to:

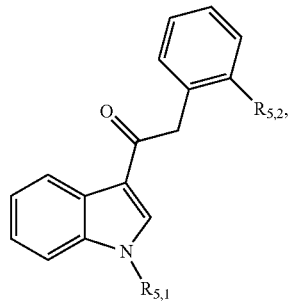

wherein $R_{5,1}$ is a $C_2$-$C_5$ substituted or unsubstituted hydrocarbon chain; and $R_{5,2}$ is selected from the group consisting of methoxy, $CH_3$ and chlorine;

wherein the antibody has a cross-reactivity presented as $B/B_0$ of ≤16%, standardised with RCS-8 as standard, and using a tracer ESC6557, against each one of the cross-reactants selected from the group consisting of JWH-203, JWH-250, JWH-250 N-(5-hydroxypentyl) metabolite, JWH-250 N-(5-carboxypentyl) metabolite, JWH-251 and RCS-8 (SR-18) at a cross-reactant concentration of 100 ng/ml, wherein RCS-8 is

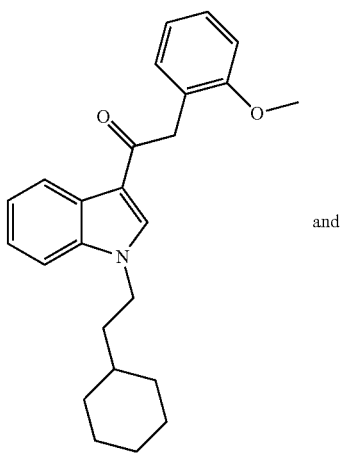 [SMILES: COc1ccccc1CC(=O)c1cn(CCC2CCCCC2)c2ccccc12]

and wherein ESC6557 is

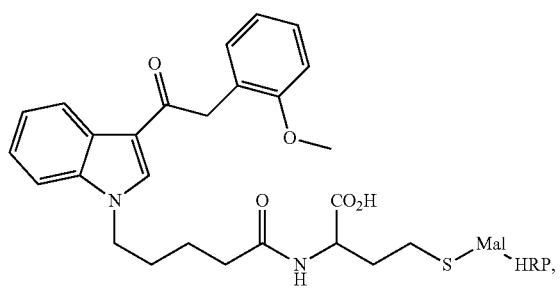

wherein Mal is maleimide,
wherein HRP is horse radish peroxidase,
wherein $B_0$ is absorbance at 450 nm at zero ng/ml standard concentration, and
wherein B is absorbance at 450 nm at predetermined variable standard concentrations.

2. The antibody of claim 1 wherein $R_{5,1}$ is selected from the group consisting of substituted ethyl; substituted butyl; pentyl; and substituted pentyl.

3. The antibody of claim 2 wherein $R_{5,1}$ is selected from the group consisting of 2-ethyl-cyclohexyl; butyryl; pentyl; and 5-hydroxypentyl.

4. The antibody of claim 1, wherein the antibody is raised from Immunogen V:

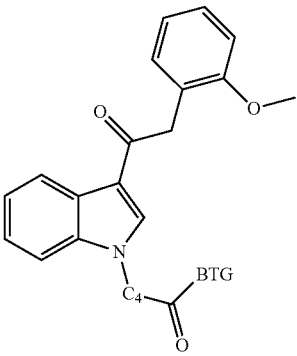

wherein $C_4$ is a $C_4$ hydrocarbon chain and BTG is bovine thyroglobulin.

5. A kit for detecting or determining at least one selected from the group consisting of at least one molecule of the JWH and RCS families and at least one metabolite thereof, the kit comprising the antibody of claim 1.

* * * * *